(12) United States Patent
Andersson et al.

(10) Patent No.: US 10,378,057 B2
(45) Date of Patent: Aug. 13, 2019

(54) METHOD TO PREDICT THE PATTERN OF LOCOMOTION IN HORSES

(71) Applicants: Lisa S. Andersson, Uppsala (SE); Leif Andersson, Uppsala (SE); Gabriella Lindgren, Knivsta (SE)

(72) Inventors: Lisa S. Andersson, Uppsala (SE); Leif Andersson, Uppsala (SE); Gabriella Lindgren, Knivsta (SE)

(73) Assignee: CAPILET GENETICS AB, Vasteras (SE)

( * ) Notice: Subject to any disclaimer, the term of this patent is extended or adjusted under 35 U.S.C. 154(b) by 0 days.

(21) Appl. No.: 15/682,124

(22) Filed: Aug. 21, 2017

(65) Prior Publication Data
US 2017/0356047 A1    Dec. 14, 2017

Related U.S. Application Data

(63) Continuation of application No. 14/795,415, filed on Jul. 9, 2015, now abandoned, which is a continuation
(Continued)

(30) Foreign Application Priority Data

May 5, 2011    (SE) ...................................... 1130034

(51) Int. Cl.
*C07H 21/04*    (2006.01)
*C12Q 1/68*    (2018.01)
(Continued)

(52) U.S. Cl.
CPC ............ *C12Q 1/6883* (2013.01); *A01K 29/00* (2013.01); *C12Q 1/6876* (2013.01);
(Continued)

(58) Field of Classification Search
None
See application file for complete search history.

(56) References Cited

FOREIGN PATENT DOCUMENTS

WO    2002092851 A2    11/2002
WO    2003046203 A2    6/2003
(Continued)

OTHER PUBLICATIONS

The Horse Genome Project (Broad Institute, EquCab1, Jan. 2007, database www.broadinstute.org/mammals/horse). (Year: 2007).*
(Continued)

*Primary Examiner* — Jeanine A Goldberg
(74) *Attorney, Agent, or Firm* — Jeffrey S. Melcher; Melcher Patent Law PLLC

(57) ABSTRACT

The present invention provides methods for predicting the pattern of locomotion in a horse including the ability of a horse to use different gaits and the ability to trot at a fast speed. The methods comprise determining in a sample of DNA obtained from a horse the presence or absence of at least one genetic marker, wherein said at least one genetic marker is located on horse chromosome 23, said marker being associated with the ability to use different gaits. The invention further provides primers that amplify markers being associated with the ability to use different gaits and hybridization probes to detect markers being associated with the ability to use different gaits and the ability to trot at a fast speed.

8 Claims, 6 Drawing Sheets

Figure 1:
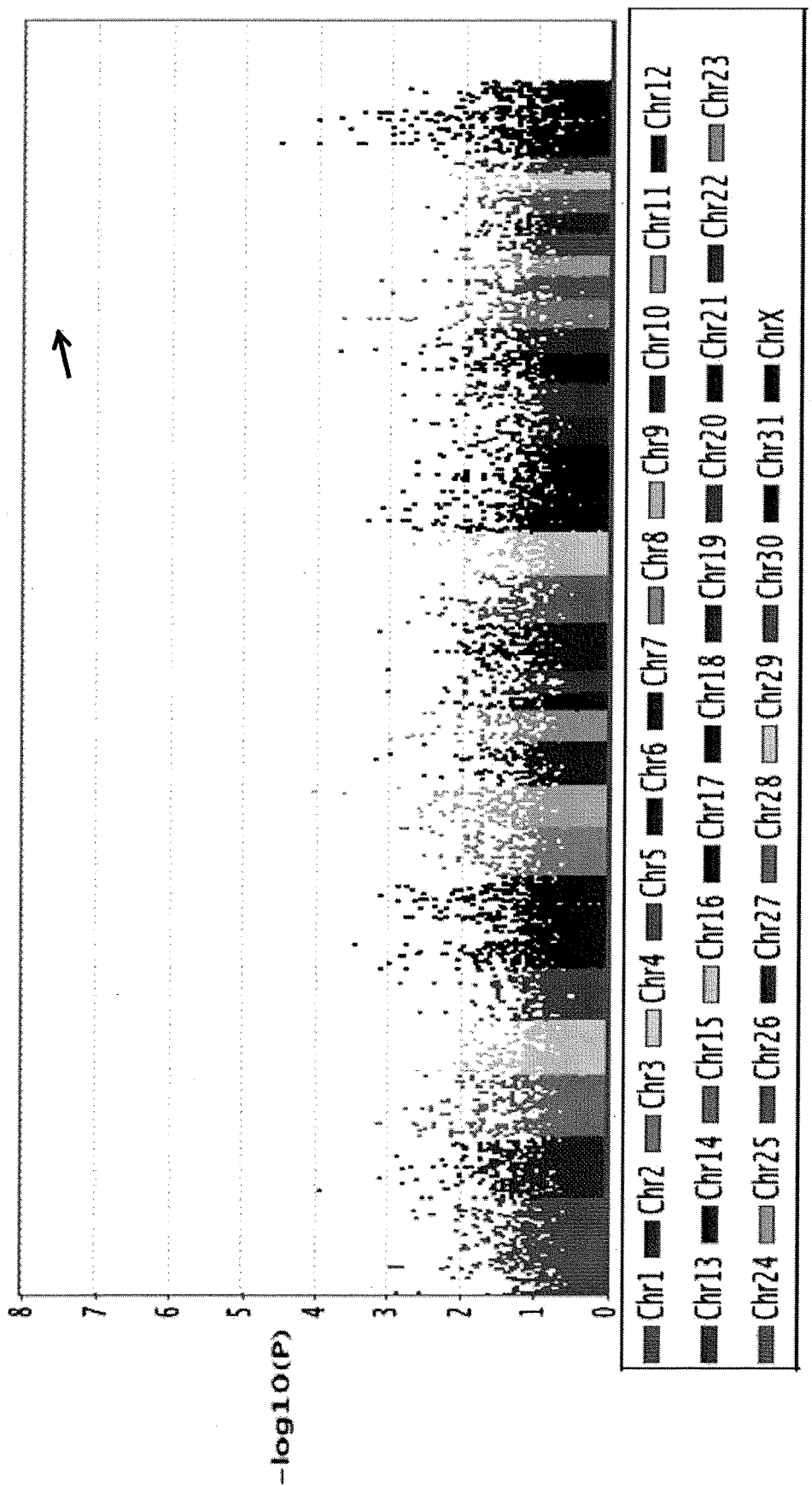

Specification includes a Sequence Listing.

```
                            301
Wild-type    A   A   D   R   T   S   A   E   P   E   S        SEQ ID NO: 130
             GCC GCC GAC CGA ACT TCG GCA GAG CCC GAG AGC      SEQ ID NO: 129

Mutant       A   A   D   R   T   Stop                         SEQ ID NO: 132
             GCC GCC GAC CGA ACT TAG GCA GAG CCC GAG AGC      SEQ ID NO: 131
```

Related U.S. Application Data of application No. 13/696,128, filed as application No. PCT/SE2012/050473 on May 4, 2012, now abandoned.

(60) Provisional application No. 61/514,749, filed on Aug. 3, 2011.

(51) Int. Cl.

| | |
|---|---|
| *C12Q 1/6883* | (2018.01) |
| *C12Q 1/6876* | (2018.01) |
| *G01N 33/68* | (2006.01) |
| *C12Q 1/6881* | (2018.01) |
| *A01K 29/00* | (2006.01) |

(52) U.S. Cl.
CPC ....... *C12Q 1/6881* (2013.01); *G01N 33/6872* (2013.01); *G01N 33/6875* (2013.01); *C12Q 2600/124* (2013.01); *C12Q 2600/156* (2013.01); *G01N 2333/4703* (2013.01)

(56) References Cited

FOREIGN PATENT DOCUMENTS

| | | |
|---|---|---|
| WO | 2006003436 A1 | 1/2006 |
| WO | 2010029527 A1 | 3/2010 |

OTHER PUBLICATIONS

Kristjansson (J. Animal Breed. Genetics, 1-11, 2014) (Year: 2014).*
Andersson et al, Nature Letter, doi: 10.1038, Nature 11399, 2012 (Year: 2012).*
Promerova et al. (Stichting International Foundation for Animal Genetics, vol. 45, ages 274-282, 2014 (Year: 2014).*
Novoa-Bravo (PLOS One, Aug. 17, 2018, 18 pages) (Year: 2018).*
Jaderkvist et al. (Livestock Science, vol. 176, pp. 33-39, 2015) (Year: 2015).*
Hirschhorn et al. (Genetics in Medicine. vol. 4, No. 2, pp. 45-61, Mar. 2002) (Year: 2002).*
Ioannidis (Nature Genetics, vol. 29, pp. 306-309, Nov. 2001) (Year: 2001).*
Swinburne J. et. al. "First Comprehensive Low-Density Horse Likage Map Based on Two 3-Generation Full-Siling, Cross-Bred Horse Reference Families," 2000, vol. 66, pp. 123-124, Genomics.
International Search Report and Written Opinion dated Jul. 26, 2012 in PCT/SE2012/050473.
Sambrook, J., Russell. D. W.. Molecular Cloning: A Laboratory Manual, the third edition, Cold Spring Harbor Laboratory Press, Cold Spring Harbor. New York, 1.31-1.38, 2001.
Sharma. R.C., et al. "A rapid procedure for isolation of RNA-free genomic DNA from mammalian cells", BioTechniques, 14. 176-178. 1993.
Sambrook et al. "Molecular Cloning, A Laboratory Manual", CSH Press, Cold Spring Harbor, 1989 or Higgins and Hames (eds.), "Nucleic acid hybridization, a practical approach", IRL Press, Oxford 1985, (in particular the chapter "Hybridization Strategy" by Britten & Davidson).
Purcell et al. 2007. PLINK: a tool set for whole-genome association and population-based linkage analyses. Am. J. Hum. Genet. 81:559-575).
Culbertson & Leeds, 2003 (Looking at mRNA decay pathways through the window of molecular evolution. Curr. Opin. Genet. Dev. 13, 207-214.
The Horse Genome Project (Broad Institute, EquCab1, Jan. 2007, database www.boradinstitute.org/mammals/horse.
Kristjansson (J. Animal Breed, Genetics, 1-11, 2014).
Andersson et al, Nature Letter, Doi: 10.1038, Nature 11399, 2012.
Promerova et. al. (Stitching International Foundation or Animal Genetics, vol. 45, pp. 274-282, 2014.).
Ionnidis (Nature Genetics, vol. 29, pp. 306-309, Nov. 2001).
Hirschhorn et. al. (Genetics in Medicine. vol. 4, No. 2, pp. 45-61, Mar. 2002).
European Search Report, issued in corresponding European Patent Application No. 12747875.8, dated Mar. 5, 2013.
Andersson, "Mutations in DMRT3 Affect Locomotion in Horses and Spinal Circuit Function in Mice," Nature, vol. 488, No. 7413, Jan. 1, 2012, pp. 642-646.
Shroder, "Candidate genes for physical performance in the horse," Veterinary Journal, Baillier Tindall, London, GB, vol. 190, No. 1, Sep. 30, 2010, pp. 39-48.
Thiruvenkadan, "Inheritance of racing performance of trotter horses: An overview," Livestock Science, Elsevier, Amsterdam, NL, vol. 124, No. 1-3, Sep. 1, 2009, pp. 163-181.
Eurasian Office Action dated Jul. 13, 2015, in Eurasian Application No. 201391408/28, with translation , pp. 1-3.

\* cited by examiner

```
                                        301
Wild-type   A   A   D   R   T   S   A   E   P   E   S    SEQ ID NO: 130
            GCC GCC GAC CGA ACT TCG GCA GAG CCC GAG AGC  SEQ ID NO: 129

Stop
Mutant      A   A   D   R   T   *   A   E   P   E   S    SEQ ID NO: 132
            GCC GCC GAC CGA ACT TAG GCA GAG CCC GAG AGC  SEQ ID NO: 131
```

Figure 3

Figure 4

SEQUENCE LISTING

<160> NUMBER OF SEQ ID NOS: 142

<210> SEQ ID NO 1
<211> LENGTH: 2196
<212> TYPE: DNA

<213> ORGANISM: Equus caballus
<220> FEATURE:
<221> NAME/KEY: CDS
<222> LOCATION: (39)..(1463)

<400> SEQUENCE: 1

```
ccgccgccag cccgccagct cttccgggag ctcagggc atg aac ggc tac ggt tcc       56
                                          Met Asn Gly Tyr Gly Ser
                                            1               5 ccc tac ctg tac atg ggc ggc ccg gtg tcg cag ccg ccg cgg gcg ccc        104
Pro Tyr Leu Tyr Met Gly Gly Pro Val Ser Gln Pro Pro Arg Ala Pro
         10                  15                  20 ttg cag cgc acg ccc aag tgc gcg cgc tgc cgc aac cac ggg gtg ctg        152
Leu Gln Arg Thr Pro Lys Cys Ala Arg Cys Arg Asn His Gly Val Leu
             25                  30                  35 tcc tgg ctc aag ggt cac aag cgc tac tgc cgc ttc aag gac tgc acc        200
Ser Trp Leu Lys Gly His Lys Arg Tyr Cys Arg Phe Lys Asp Cys Thr
         40                  45                  50 tgc gag aag tgc atc ctc atc atc gag cgg cag agg gtc atg gcg gcg        248
Cys Glu Lys Cys Ile Leu Ile Ile Glu Arg Gln Arg Val Met Ala Ala
 55                  60                  65                  70 cag gtg gcg ctg cgc cgg cag caa gct aac gag agc ctc gag agc ctc        296
Gln Val Ala Leu Arg Arg Gln Gln Ala Asn Glu Ser Leu Glu Ser Leu
                 75                  80                  85 att ccc gac tcg ctg cgt gct ctg ccc ggc ccc ccg ccg ggg gac            344
Ile Pro Asp Ser Leu Arg Ala Leu Pro Gly Pro Pro Pro Gly Asp
             90                  95                 100 gcc gcc gct gcc gcc ccg cag ccg ccc acc tcg cag ccg tct cag            392
Ala Ala Ala Ala Ala Pro Gln Pro Pro Thr Ser Gln Pro Ser Gln
         105                 110                 115 ccg ccg ccg ccg cag cgt ccc gcc gcc gag ttg gct gcg gcc gcc gcg        440
Pro Pro Pro Pro Gln Arg Pro Ala Ala Glu Leu Ala Ala Ala Ala
 120                 125                 130 ctg cgc tgg gcc acc gag ccg cag ccc ggg gcg ctg cag gcg cag ctc        488
Leu Arg Trp Ala Thr Glu Pro Gln Pro Gly Ala Leu Gln Ala Gln Leu
135                 140                 145                 150 gac aag cca gat ttg act gag gag cga ctt ggg gac ggc agc tcc gca        536
Asp Lys Pro Asp Leu Thr Glu Glu Arg Leu Gly Asp Gly Ser Ser Ala
                155                 160                 165 gac aac aca gag acc ttc agc gac aaa gac acc gac cag agg agc tcc        584
Asp Asn Thr Glu Thr Phe Ser Asp Lys Asp Thr Asp Gln Arg Ser Ser
            170                 175                 180 cca gat gtg gtg aaa agt aag ggc tgc ttc acc ccg gag agc ccc gag        632
Pro Asp Val Val Lys Ser Lys Gly Cys Phe Thr Pro Glu Ser Pro Glu
        185                 190                 195 gtc gtg tct gtg gat gaa ggc ggg tat gcg gtc cag aag aac gga ggc        680
Val Val Ser Val Asp Glu Gly Gly Tyr Ala Val Gln Lys Asn Gly Gly
    200                 205                 210 acc tcc gag agc cgc ccc gac agt ccc aag tac cac ggg gaa cag aat        728
Thr Ser Glu Ser Arg Pro Asp Ser Pro Lys Tyr His Gly Glu Gln Asn
215                 220                 225                 230 cac ctc ctg atc gag ggc ccc tcg ggg acc gtt tct ctg ccc ttc agc        776
His Leu Leu Ile Glu Gly Pro Ser Gly Thr Val Ser Leu Pro Phe Ser
                235                 240                 245 ttg aaa gcc aac aga ccg ccc ctg gaa gtg tta aaa aaa atc ttc ccc        824
Leu Lys Ala Asn Arg Pro Pro Leu Glu Val Leu Lys Lys Ile Phe Pro
            250                 255                 260 aac cag aag ccc acg gtg ctg gag ctc atc ctg aag ggc tgt ggg ggc        872
Asn Gln Lys Pro Thr Val Leu Glu Leu Ile Leu Lys Gly Cys Gly Gly
        265                 270                 275
```

```
gac ctg gtg agc gcc gtg gag gtc ctc ctc tcc agc cgc tcc tcg gcc    920
Asp Leu Val Ser Ala Val Glu Val Leu Leu Ser Ser Arg Ser Ser Ala
        280                 285                 290 tcg gcc gcc gac cga act tcg gca gag ccc gag agc ctc gtg ttg ccc    968
Ser Ala Ala Asp Arg Thr Ser Ala Glu Pro Glu Ser Leu Val Leu Pro
295                 300                 305                 310 tcc aac ggg cac atc ttt gaa cac acc ttg agc tca tac ccc atc tcc    1016
Ser Asn Gly His Ile Phe Glu His Thr Leu Ser Ser Tyr Pro Ile Ser
            315                 320                 325 tct tcc aaa tgg tcc gtg gga tcg gcc ttc agg gtc cca gac acg ttg    1064
Ser Ser Lys Trp Ser Val Gly Ser Ala Phe Arg Val Pro Asp Thr Leu
                330                 335                 340 agg ttt tcc gca gac tct agt aac gtt gtc ccc aac ccc ttg gcc gtg    1112
Arg Phe Ser Ala Asp Ser Ser Asn Val Val Pro Asn Pro Leu Ala Val
                    345                 350                 355 ccc ctg cag cat cct ttc ccc cag ccg ccc cgg tac cct ctg atg ctg    1160
Pro Leu Gln His Pro Phe Pro Gln Pro Pro Arg Tyr Pro Leu Met Leu
        360                 365                 370 agg aat act ttg gca aga aac cag tcg agc ccc ttc ctg ccc aat gat    1208
Arg Asn Thr Leu Ala Arg Asn Gln Ser Ser Pro Phe Leu Pro Asn Asp
375                 380                 385                 390 gtc acc ctg tgg aac acc atg acg ctg cag cag cag tac cag ctg agg    1256
Val Thr Leu Trp Asn Thr Met Thr Leu Gln Gln Gln Tyr Gln Leu Arg
            395                 400                 405 tcc cag tac gtc agc cct ttc ccc ggg agc tcg ccc agc gtc ttc aga    1304
Ser Gln Tyr Val Ser Pro Phe Pro Gly Ser Ser Pro Ser Val Phe Arg
                410                 415                 420 agc tcg cct gtc ctt ccc acg cgc gcc ccc gaa gac cct cgg atc tcc    1352
Ser Ser Pro Val Leu Pro Thr Arg Ala Pro Glu Asp Pro Arg Ile Ser
                    425                 430                 435 atc cct gac gat ggg tgt ccg att gtg tca aag cag tct ctt tac acc    1400
Ile Pro Asp Asp Gly Cys Pro Ile Val Ser Lys Gln Ser Leu Tyr Thr
        440                 445                 450 gag gat gac tat gac gag agg tcc gac tcc tca gac tct aga ata ctc    1448
Glu Asp Asp Tyr Asp Glu Arg Ser Asp Ser Ser Asp Ser Arg Ile Leu
455                 460                 465                 470 aac aca tca tct taa agtggtaccg ggtggctggt gaccaggtga cattttctgt    1503
Asn Thr Ser Ser gcatttgaac tctgaccccc tgccctcccc aggagaggcc tcgtcctgtg tatacccttt    1563
ccttctgttt gacaaagtga ctgtgcttga ttctatacct tagcaataaa acataacttt    1623
atttaatttc ttgcacttca ctggaaaatg ccaaatagct ctgctctgcg gctttagtgc    1683
tgaatgttta ttgtaaaaga gagtctaatg ctaagaatag tcttgggaaa gctgggtcca    1743
cggaagattt atttggggat ggaaagctga aggtcagcct tgctcctaaa ctcaacctgg    1803
aatgttcaat aaaatagtat acttgaatgc agttttgtaa aaaaggattc ctcaggatat    1863
ttgaaaccta aggaagtgg tttggttgca aatggaccag aaacagggac attatattct    1923
taggctaaaa accttgcatt taaaagagag actgcactta agaatagagt gaactgctca    1983
catgcttatt taagcttgga cagttttcag agacaaattc cattaagaat tattctttc    2043 acatgaccga atcgaaacat gtgtaatgtc aatgtaaaac caatcacagc tgtgaactgc    2103
atgaaatgta ttgtgaaatg aacacaagat taagctttgt caggttaatg tagcatgcta    2163
aggactctag aaaaaaataa actaaggaga tga                                 2196

<210> SEQ ID NO 2
<211> LENGTH: 474
<212> TYPE: PRT
```

<213> ORGANISM: Equus caballus

<400> SEQUENCE: 2

Met Asn Gly Tyr Gly Ser Pro Tyr Leu Tyr Met Gly Gly Pro Val Ser
1               5                   10                  15

Gln Pro Pro Arg Ala Pro Leu Gln Arg Thr Pro Lys Cys Ala Arg Cys
            20                  25                  30

Arg Asn His Gly Val Leu Ser Trp Leu Lys Gly His Lys Arg Tyr Cys
        35                  40                  45

Arg Phe Lys Asp Cys Thr Cys Glu Lys Cys Ile Leu Ile Ile Glu Arg
    50                  55                  60

Gln Arg Val Met Ala Ala Gln Val Ala Leu Arg Arg Gln Gln Ala Asn
65                  70                  75                  80

Glu Ser Leu Glu Ser Leu Ile Pro Asp Ser Leu Arg Ala Leu Pro Gly
                85                  90                  95

Pro Pro Pro Pro Gly Asp Ala Ala Ala Ala Pro Gln Pro Pro Pro
            100                 105                 110

Thr Ser Gln Pro Ser Gln Pro Pro Pro Gln Arg Pro Ala Ala Glu
                115                 120                 125

Leu Ala Ala Ala Ala Leu Arg Trp Ala Thr Glu Pro Gln Pro Gly
        130                 135                 140

Ala Leu Gln Ala Gln Leu Asp Lys Pro Asp Leu Thr Glu Glu Arg Leu
145                 150                 155                 160

Gly Asp Gly Ser Ser Ala Asp Asn Thr Glu Thr Phe Ser Asp Lys Asp
                165                 170                 175

Thr Asp Gln Arg Ser Ser Pro Asp Val Val Lys Ser Lys Gly Cys Phe
            180                 185                 190

Thr Pro Glu Ser Pro Glu Val Val Ser Val Asp Glu Gly Gly Tyr Ala
        195                 200                 205

Val Gln Lys Asn Gly Gly Thr Ser Glu Ser Arg Pro Asp Ser Pro Lys
210                 215                 220

Tyr His Gly Glu Gln Asn His Leu Leu Ile Glu Gly Pro Ser Gly Thr
225                 230                 235                 240

Val Ser Leu Pro Phe Ser Leu Lys Ala Asn Arg Pro Pro Leu Glu Val
                245                 250                 255

Leu Lys Lys Ile Phe Pro Asn Gln Lys Pro Thr Val Leu Glu Leu Ile
            260                 265                 270

Leu Lys Gly Cys Gly Gly Asp Leu Val Ser Ala Val Glu Val Leu Leu
        275                 280                 285

Ser Ser Arg Ser Ser Ala Ser Ala Ala Asp Arg Thr Ser Ala Glu Pro
290                 295                 300

Glu Ser Leu Val Leu Pro Ser Asn Gly His Ile Phe Glu His Thr Leu
305                 310                 315                 320

Ser Ser Tyr Pro Ile Ser Ser Ser Lys Trp Ser Val Gly Ser Ala Phe
                325                 330                 335

Arg Val Pro Asp Thr Leu Arg Phe Ser Ala Asp Ser Ser Asn Val Val
            340                 345                 350

Pro Asn Pro Leu Ala Val Pro Leu Gln His Pro Phe Pro Gln Pro Pro
        355                 360                 365

Arg Tyr Pro Leu Met Leu Arg Asn Thr Leu Ala Arg Asn Gln Ser Ser
    370                 375                 380

Pro Phe Leu Pro Asn Asp Val Thr Leu Trp Asn Thr Met Thr Leu Gln
385                 390                 395                 400

-continued

```
Gln Gln Tyr Gln Leu Arg Ser Gln Tyr Val Ser Pro Phe Pro Gly Ser
            405                 410                 415

Ser Pro Ser Val Phe Arg Ser Pro Val Leu Pro Thr Arg Ala Pro
        420                 425                 430

Glu Asp Pro Arg Ile Ser Ile Pro Asp Asp Gly Cys Pro Ile Val Ser
    435                 440                 445

Lys Gln Ser Leu Tyr Thr Glu Asp Asp Tyr Asp Glu Arg Ser Asp Ser
    450                 455                 460

Ser Asp Ser Arg Ile Leu Asn Thr Ser Ser
465                 470

<210> SEQ ID NO 3
<211> LENGTH: 2196
<212> TYPE: DNA
<213> ORGANISM: Equus caballus
<220> FEATURE:
<221> NAME/KEY: CDS
<222> LOCATION: (39)..(941)

<400> SEQUENCE: 3
```

| | |
|---|---|
| ccgccgccag cccgccagct cttccgggag ctcagggc atg aac ggc tac ggt tcc<br>                                                               Met Asn Gly Tyr Gly Ser<br>                                                                     1                5 | 56 |

```
ccc tac ctg tac atg ggc ggc ccg gtg tcg cag ccg ccg cgg gcg ccc      104
Pro Tyr Leu Tyr Met Gly Gly Pro Val Ser Gln Pro Pro Arg Ala Pro
            10                  15                  20 ttg cag cgc acg ccc aag tgc gcg cgc tgc cgc aac cac ggg gtg ctg      152
Leu Gln Arg Thr Pro Lys Cys Ala Arg Cys Arg Asn His Gly Val Leu
        25                  30                  35 tcc tgg ctc aag ggt cac aag cgc tac tgc cgc ttc aag gac tgc acc      200
Ser Trp Leu Lys Gly His Lys Arg Tyr Cys Arg Phe Lys Asp Cys Thr
    40                  45                  50 tgc gag aag tgc atc ctc atc atc gag cgg cag agg gtc atg gcg gcg      248
Cys Glu Lys Cys Ile Leu Ile Ile Glu Arg Gln Arg Val Met Ala Ala
55                  60                  65                  70 cag gtg gcg ctg cgc cgg cag caa gct aac gag agc ctc gag agc ctc      296
Gln Val Ala Leu Arg Arg Gln Gln Ala Asn Glu Ser Leu Glu Ser Leu
                75                  80                  85 att ccc gac tcg ctg cgt gct ctg ccc ggc ccc ccg ccg ggg gac          344
Ile Pro Asp Ser Leu Arg Ala Leu Pro Gly Pro Pro Pro Gly Asp
            90                  95                  100 gcc gcc gct gcc gcc ccg cag ccg ccg ccc acc tcg cag ccg tct cag      392
Ala Ala Ala Ala Ala Pro Gln Pro Pro Pro Thr Ser Gln Pro Ser Gln
            105                 110                 115 ccg ccg ccg ccg cag cgt ccc gcc gcc gag ttg gct gcg gcc gcc gcg      440
Pro Pro Pro Pro Gln Arg Pro Ala Ala Glu Leu Ala Ala Ala Ala Ala
        120                 125                 130 ctg cgc tgg gcc acc gag ccg cag ccc ggg gcg ctg cag gcg cag ctc      488
Leu Arg Trp Ala Thr Glu Pro Gln Pro Gly Ala Leu Gln Ala Gln Leu
135                 140                 145                 150 gac aag cca gat ttg act gag gag cga ctt ggg gac ggc agc tcc gca      536
Asp Lys Pro Asp Leu Thr Glu Glu Arg Leu Gly Asp Gly Ser Ser Ala
                155                 160                 165 gac aac aca gag acc ttc agc gac aaa gac acc gac cag agg agc tcc      584
Asp Asn Thr Glu Thr Phe Ser Asp Lys Asp Thr Asp Gln Arg Ser Ser
            170                 175                 180 cca gat gtg gtg aaa agt aag ggc tgc ttc acc ccg gag agc ccc gag      632
Pro Asp Val Val Lys Ser Lys Gly Cys Phe Thr Pro Glu Ser Pro Glu
        185                 190                 195 gtc gtg tct gtg gat gaa ggc ggg tat gcg gtc cag aag aac gga ggc      680
```

|  |  |  |  |  |  |  |  |  |  |  |  |  |  |  |  |
|---|---|---|---|---|---|---|---|---|---|---|---|---|---|---|---|
| Val | Val | Ser | Val | Asp | Glu | Gly | Gly | Tyr | Ala | Val | Gln | Lys | Asn | Gly | Gly |
|  | 200 |  |  |  | 205 |  |  |  | 210 |  |  |  |  |  |  |

```
acc tcc gag agc cgc ccc gac agt ccc aag tac cac ggg gaa cag aat    728
Thr Ser Glu Ser Arg Pro Asp Ser Pro Lys Tyr His Gly Glu Gln Asn
215                 220                 225                 230 cac ctc ctg atc gag ggc ccc tcg ggg acc gtt tct ctg ccc ttc agc    776
His Leu Leu Ile Glu Gly Pro Ser Gly Thr Val Ser Leu Pro Phe Ser
                235                 240                 245 ttg aaa gcc aac aga ccg ccc ctg gaa gtg tta aaa aaa atc ttc ccc    824
Leu Lys Ala Asn Arg Pro Pro Leu Glu Val Leu Lys Lys Ile Phe Pro
        250                 255                 260 aac cag aag ccc acg gtg ctg gag ctc atc ctg aag ggc tgt ggg ggc    872
Asn Gln Lys Pro Thr Val Leu Glu Leu Ile Leu Lys Gly Cys Gly Gly
                265                 270                 275 gac ctg gtg agc gcc gtg gag gtc ctc ctc tcc agc cgc tcc tcg gcc    920
Asp Leu Val Ser Ala Val Glu Val Leu Leu Ser Ser Arg Ser Ser Ala
            280                 285                 290 tcg gcc gcc gac cga act tag gcagagcccg agagcctcgt gttgccctcc       971
Ser Ala Ala Asp Arg Thr
295                 300 aacgggcaca tctttgaaca caccttgagc tcatacccca tctcctcttc caaatggtcc  1031
gtgggatcgg ccttcagggt cccagacacg ttgaggtttt ccgcagactc tagtaacgtt  1091
gtccccaacc cctggccgt gccctgcag catcctttcc cccagccgcc ccggtaccct    1151
ctgatgctga ggaatacttt ggcaagaaac cagtcgagcc ccttcctgcc caatgatgtc  1211
accctgtgga acaccatgac gctgcagcag cagtaccagc tgaggtccca gtacgtcagc  1271
cctttccccg ggagctcgcc cagcgtcttc agaagctcgc ctgtccttcc cacgcgcgcc  1331
cccgaagacc ctcggatctc catccctgac gatgggtgtc cgattgtgtc aaagcagtct  1391
ctttacaccg aggatgacta tgacgagagg tccgactcct cagactctag aatactcaac  1451
acatcatctt aaagtggtac cgggtggctg gtgaccaggt gacattttct gtgcatttga  1511
actctgaccc cctgccctcc ccaggagagg cctcgtcctg tgtataccct ttccttctgt  1571
ttgacaaagt gactgtgctt gattctatac cttagcaata aaaacataac ttatttaatt  1631
tcttgcactt cactggaaaa tgccaaatag ctctgctctg cggctttagt gctgaatgtt  1691
tattgtaaaa gagagtctaa tgctaagaat agtcttggga aagctgggtc cacggaagat  1751
ttatttgggg atggaaagct gaaggtcagc cttgctccta aactcaacct ggaatgttca  1811
ataaaatagt atacttgaat gcagttttgt aaaaaaggat tcctcaggat atttgaaacc  1871
taaaggaagt ggtttggttg caaatggacc agaaacaggg acattatatt cttaggctaa  1931
aaaccttgca tttaaaagag agactgcact taagaataga gtgaactgct cacatgctta  1991
tttaagcttg gacagttttc agagacaaat tccattaaga attattcttt tcacatgacc  2051
gaatcgaaac atgtgtaatg tcaatgtaaa accaatcaca gctgtgaact gcatgaaatg  2111
tattgtgaaa tgaacacaag attaagcttt gtcaggttaa tgtagcatgc taaggactct  2171
agaaaaaaat aaactaagga gatga                                       2196
```

<210> SEQ ID NO 4
<211> LENGTH: 300
<212> TYPE: PRT
<213> ORGANISM: Equus caballus
<400> SEQUENCE: 4

```
Met Asn Gly Tyr Gly Ser Pro Tyr Leu Tyr Met Gly Gly Pro Val Ser
1               5                   10                  15
```

Gln Pro Pro Arg Ala Pro Leu Gln Arg Thr Pro Lys Cys Ala Arg Cys
            20                  25                  30

Arg Asn His Gly Val Leu Ser Trp Leu Lys Gly His Lys Arg Tyr Cys
        35                  40                  45

Arg Phe Lys Asp Cys Thr Cys Glu Lys Cys Ile Leu Ile Ile Glu Arg
50                  55                  60

Gln Arg Val Met Ala Ala Gln Val Ala Leu Arg Arg Gln Gln Ala Asn
65                  70                  75                  80

Glu Ser Leu Glu Ser Leu Ile Pro Asp Ser Leu Arg Ala Leu Pro Gly
                85                  90                  95

Pro Pro Pro Pro Gly Asp Ala Ala Ala Ala Pro Gln Pro Pro Pro
            100                 105                 110

Thr Ser Gln Pro Ser Gln Pro Pro Pro Gln Arg Pro Ala Ala Glu
            115                 120                 125

Leu Ala Ala Ala Ala Leu Arg Trp Ala Thr Glu Pro Gln Pro Gly
130                 135                 140

Ala Leu Gln Ala Gln Leu Asp Lys Pro Asp Leu Thr Glu Glu Arg Leu
145                 150                 155                 160

Gly Asp Gly Ser Ser Ala Asp Asn Thr Glu Thr Phe Ser Asp Lys Asp
                165                 170                 175

Thr Asp Gln Arg Ser Ser Pro Asp Val Val Lys Ser Lys Gly Cys Phe
            180                 185                 190

Thr Pro Glu Ser Pro Glu Val Val Ser Val Asp Glu Gly Gly Tyr Ala
            195                 200                 205

Val Gln Lys Asn Gly Gly Thr Ser Glu Ser Arg Pro Asp Ser Pro Lys
210                 215                 220

Tyr His Gly Glu Gln Asn His Leu Leu Ile Glu Gly Pro Ser Gly Thr
225                 230                 235                 240

Val Ser Leu Pro Phe Ser Leu Lys Ala Asn Arg Pro Pro Leu Glu Val
                245                 250                 255

Leu Lys Lys Ile Phe Pro Asn Gln Lys Pro Thr Val Leu Glu Leu Ile
            260                 265                 270

Leu Lys Gly Cys Gly Gly Asp Leu Val Ser Ala Val Glu Val Leu Leu
            275                 280                 285

Ser Ser Arg Ser Ser Ala Ser Ala Ala Asp Arg Thr
290                 295                 300

<210> SEQ ID NO 5
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is c or t

<400> SEQUENCE: 5
ttgttggggt cttatgcaaa gtgcagaaat agtcttttgg aaaaacgtac ngtttgcact    60
attttcttat ttctattcac ccttaatgtg aaccattcca a                        101

<210> SEQ ID NO 6
<211> LENGTH: 101
<212> TYPE: DNA
<213> ORGANISM: Equus caballus
<220> FEATURE:
<221> NAME/KEY: misc_feature
<222> LOCATION: (51)..(51)

<223> OTHER INFORMATION: n is a or g

<400> SEQUENCE: 6
agaaatgata tataaaaatt acgaatgcct cttagacaga atccttatgt ntggcacaga    60
agtatttagt tcgcttaaca gatattgagt gcttatatga g    101

<210> SEQ ID NO 7
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is c or t

<400> SEQUENCE: 7
ctcttccttg catcctatcc ccctagtgtc gcaagggaag ttgtgagaga ngagcttgta    60
gatctgctct agaaaatagg cctgttttct taagaaaccg t    101

<210> SEQ ID NO 8
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is g or c

<400> SEQUENCE: 8
cagagtgccg gtctgtggct gtgggcgctg acgagcacat ggacaacatt ntcgtgtacc    60 acagggctc caggtcctgt aaggatgctg ctgtggggac a    101

<210> SEQ ID NO 9
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is a or g

<400> SEQUENCE: 9
agaactcatt caaaaccacc aggcttacta ggcttttta aatagacttg nctttgaact    60
tctaagtgca ggatctaaaa ccactggcga aatttctgga a    101

<210> SEQ ID NO 10
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is t or g

<400> SEQUENCE: 10
ttacctgcat gcctctcccc ctaaaccatt tctagcatgt gtgggcagag ngggcatcgt    60
gctgccctgc tcactggatc actctgggaa cgtttccttc a    101

<210> SEQ ID NO 11
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is t or c

<400> SEQUENCE: 11
aaggatatgg tgagtctgac ctacagacac tgtccccggt ctgtacaaag ngcccaagtg    60
gtgacaaagc atccctcgcc tgcccctga gctgttacct g                        101

<210> SEQ ID NO 12
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is c or t

<400> SEQUENCE: 12
aacgccaaag ccagccaggt gactgcgctt gcttcctggg ctcatgctca nactgctgtg    60
acccgcacag gtgcccacgc cacacttccc accgctcggc a                       101

<210> SEQ ID NO 13
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is a or g

<400> SEQUENCE: 13
gcttgcttcc tgggctcatg ctcacactgc tgtgacccgc acaggtgccc ncgccacact    60
tcccaccgct cggcactcac tcatggccca gccccgagtc c                       101

<210> SEQ ID NO 14
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is a or c

<400> SEQUENCE: 14
actgaatgta tacattttgt gcctgaactc accagcaaac agaaggcaga naaccaaggg    60
ttgaaggctg gagctgtcac agtagaagtt gagccagcag g                       101

<210> SEQ ID NO 15
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is g or c

<400> SEQUENCE: 15
cattttgtgc ctgaactcac cagcaaacag aaggcagaaa accaagggtt naaggctgga    60
gctgtcacag tagaagttga gccagcagga atttgctggc c                       101

<210> SEQ ID NO 16
<211> LENGTH: 101
<212> TYPE: DNA
<213> ORGANISM: Equus caballus
<220> FEATURE:

<221> NAME/KEY: misc_feature
<222> LOCATION: (51)..(51)
<223> OTHER INFORMATION: n is c or t

<400> SEQUENCE: 16
tcactctaat caagttgcta tcaccattca cacaattgtc caggatagta ntgggacccc    60
agaaagatca cgccgctcca ttcccatttc ccacttgttc c                       101

<210> SEQ ID NO 17
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is g or a

<400> SEQUENCE: 17
ctgggctgaa acaggtggtc ctgctttccc cgcctgcctg gtcaggctgc nctcttctcc    60
cctccccagg cttaagtcac ttcatgcaga acccttata c                        101

<210> SEQ ID NO 18
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is g or c

<400> SEQUENCE: 18
ccagcattct ccgctttcaa ctttctcccg ctcctccaat ccaaactgga nttagcatca    60
gctacccaca atgatcaagc attttctgtg tggcaggcct g                       101

<210> SEQ ID NO 19
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is c or a

<400> SEQUENCE: 19
aggcaagaag cgataggcaa aaggcagcaa gagctggacc tgcagatttg naagttctct    60
ggagccagta ggtggaaacc tcatcagcaa atgaacgcag g                       101

<210> SEQ ID NO 20
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is t or c

<400> SEQUENCE: 20
ccacactgag agtcttattt gctgatagaa atgcagagac ttctcttttc ngaggctttc    60
aacctcgtac ttaattctcc taagtgagaa agaaaccact c                       101

<210> SEQ ID NO 21
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is c or t

<400> SEQUENCE: 21
accagcggga gactgaggct gcgagcgccg caaagacggg tgccgcatct ntggccagcc    60
cggagcgcac gcggccgccg gagctgcggg accaaggacc g    101

<210> SEQ ID NO 22
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is c or t

<400> SEQUENCE: 22
ccgtctcagc cgccgccgcc gcagcgtccc gccgccgagt tggctgcggc ngccgcgctg    60
cgctgggcca ccgagccgca gcccggggcg ctgcaggcgc a    101

<210> SEQ ID NO 23
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is c or a

<400> SEQUENCE: 23
ggaggtcctc ctctccagcc gctcctcggc ctcggccgcc gaccgaactt nggcagagcc    60
cgagagcctc gtgttgccct ccaacgggca catctttgaa c    101

<210> SEQ ID NO 24
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is c or g

<400> SEQUENCE: 24
ctctccagcc gctcctcggc ctcggccgcc gaccgaactt cggcagagcc ngagagcctc    60
gtgttgccct ccaacgggca catctttgaa cacaccttga g    101

<210> SEQ ID NO 25
<211> LENGTH: 101
<212> TYPE: DNA
<213> ORGANISM: Equus caballus
<220> FEATURE:
<221> NAME/KEY: misc_feature
<222> LOCATION: (51)..(51)
<223> OTHER INFORMATION: n is a or t

<400> SEQUENCE: 25
ggcctggccc ctagggcatt gaagggctgg ggagagtcac atgtactccc nctgtggcct    60
gaagacctac ctggagggaa accagcttgc ttaggggcc t    101

<210> SEQ ID NO 26
<211> LENGTH: 26
<212> TYPE: DNA

```
<213> ORGANISM: Artificial Sequence
<220> FEATURE:
<223> OTHER INFORMATION: Primer

<400> SEQUENCE: 26
gcaaagtgca gaaatagtct tttgga                                        26

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
cactcttttg gaatggttca cattaagg                                      28

<210> SEQ ID NO 28
<211> LENGTH: 18
<212> TYPE: DNA
<213> ORGANISM: Artificial Sequence
<220> FEATURE:
<223> OTHER INFORMATION: Reporter

<400> SEQUENCE: 28
tagtgcaaac ggtacgtt                                                 18

<210> SEQ ID NO 29
<211> LENGTH: 21
<212> TYPE: DNA
<213> ORGANISM: Artificial Sequence
<220> FEATURE:
<223> OTHER INFORMATION: Reporter

<400> SEQUENCE: 29
aaatagtgca aacagtacgt t                                             21

<210> SEQ ID NO 30
<211> LENGTH: 17
<212> TYPE: DNA
<213> ORGANISM: Artificial Sequence
<220> FEATURE:
<223> OTHER INFORMATION: Primer

<400> SEQUENCE: 30
cctctccagc cgctcct                                                  17

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tcaaagatgt gcccgttgga                                               20

<210> SEQ ID NO 32
<211> LENGTH: 13
<212> TYPE: DNA
<213> ORGANISM: Artificial Sequence
<220> FEATURE:
<223> OTHER INFORMATION: Reporter

<400> SEQUENCE: 32
ctgccgaagt tcg                                                      13
```

<210> SEQ ID NO 33
<211> LENGTH: 15
<212> TYPE: DNA
<213> ORGANISM: Artificial Sequence
<220> FEATURE:
<223> OTHER INFORMATION: Reporter

<400> SEQUENCE: 33
ctctgcctaa gttcg                                                         15

<210> SEQ ID NO 34
<211> LENGTH: 32
<212> TYPE: DNA
<213> ORGANISM: Artificial Sequence
<220> FEATURE:
<223> OTHER INFORMATION: Probe

<400> SEQUENCE: 34
ggatcctcga gaacaatgta acaatttcgc cc                                      32

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
cataccagct tgccacact                                                     19

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gaggagagag agctcgtgga                                                    20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ctaatggaga cccgcagaag                                                    20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gccggaactc ctttatcctc                                                    20

<210> SEQ ID NO 39
<211> LENGTH: 20
<212> TYPE: DNA
<213> ORGANISM: Artificial Sequence
<220> FEATURE:

<223> OTHER INFORMATION: Primer

<400> SEQUENCE: 39
gagaagtggc ggggaattat                                        20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
gccccacgac tttattctca                                        20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
tgcagacgag agaccaaatg                                        20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
aaacccagaa gtgcctgaga                                        20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
gcggacagtg gctataggag                                        20

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
aatacattgt ccccaccctt c                                      21

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
atgggatttg agctgagtgg                                        20

```
<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
aagcctgatg ctgagaagga                                              20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
ttgcatgcac acaattttcc                                              20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ctgggggttt ctgagttctg                                              20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
gcaacccagg ttatcccttt                                              20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
tcaccttctg cacttgcatt                                              20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
aagtcgactg aggggctctt                                              20

<210> SEQ ID NO 52
<211> LENGTH: 20
<212> TYPE: DNA
<213> ORGANISM: Artificial Sequence
<220> FEATURE:
<223> OTHER INFORMATION: Primer
```

```
<400> SEQUENCE: 52
accttggccc agataggttt                                               20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
tccccaggaa catacagctc                                               20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
tggaaaggat ttgaggatgc                                               20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
gcttctggcc tcacgaaata                                               20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
tggcatgaag acaccacaat                                               20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
agccccagta cagaccacac                                               20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
gggaagtcgc ctacactgaa                                               20

<210> SEQ ID NO 59
<211> LENGTH: 20
```

```
<212> TYPE: DNA
<213> ORGANISM: Artificial Sequence
<220> FEATURE:
<223> OTHER INFORMATION: Primer

<400> SEQUENCE: 59
gaggatccgt gggatacaga                                               20

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
agcaagtctc ctgagcaagc                                               20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
cagaggacac atctgcctga                                               20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
caaaaccatc ctggaaatgg                                               20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
agactggccc tgagctaaca                                               20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
tgtcagctgc agaatggaag                                               20

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
```
agactggccc tgagctaaca                                          20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
ctgaaggtgc cctctacagc                                          20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
ttacctgccc ctttgttttg                                          20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
catctttgcc cctcagactc                                          20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
ttacgtggca cccctacttc                                          20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
agcctggact ctgtccttga                                          20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
tgctgccctc tgtctatgtg                                          20

<210> SEQ ID NO 72
<211> LENGTH: 20
<212> TYPE: DNA
<213> ORGANISM: Artificial Sequence

```
<220> FEATURE:
<223> OTHER INFORMATION: Primer

<400> SEQUENCE: 72
aaagtaacga tgcggtggac                                               20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
aaatggctgt gccgttttac                                               20

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
ctgtgtgacc aagctctcca                                               20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
gaaaatgctg acgtgctgaa                                               20

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
cttgctgcct tttgcctatc                                               20

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
gcagagcgac ctggagatag                                               20

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
ggccttagag ggacacatga                                               20
```

```
<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
cctctcaccc agacaccatt                                               20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
agttggcaaa caacaggaca                                               20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
aagtcctttc ttgggggcta                                               20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
ggtccatcgt tgaccaaaat                                               20

<210> SEQ ID NO 83
<211> LENGTH: 20
<212> TYPE: DNA
<213> ORGANISM: Artificial Sequence
<220> FEATURE:
<223> OTHER INFORMATION: Primeer

<400> SEQUENCE: 83
agtcctttct tgggggctaa                                               20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
acggcaccac catcatctat                                               20

<210> SEQ ID NO 85
<211> LENGTH: 20
<212> TYPE: DNA
<213> ORGANISM: Artificial Sequence
<220> FEATURE:
<223> OTHER INFORMATION: Primer
```

```
<400> SEQUENCE: 85
gccccaactt aagaccctct                                           20

<210> SEQ ID NO 86
<211> LENGTH: 18
<212> TYPE: DNA
<213> ORGANISM: Artificial Sequence
<220> FEATURE:
<223> OTHER INFORMATION: Primer

<400> SEQUENCE: 86
ccgcgctgct taggagtc                                             18

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
gccccaactt aagaccctct                                           20

<210> SEQ ID NO 88
<211> LENGTH: 19
<212> TYPE: DNA
<213> ORGANISM: Artificial Sequence
<220> FEATURE:
<223> OTHER INFORMATION: Primer

<400> SEQUENCE: 88
tacctggctt gtcgagctg                                            19

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
gagcacgctc agaccctatc                                           20

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
aaagagctcc gaagttttg c                                          21

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
ctccttccaa gaagcctgtg                                           20

<210> SEQ ID NO 92
```

```
<211> LENGTH: 20
<212> TYPE: DNA
<213> ORGANISM: Artificial Sequence
<220> FEATURE:
<223> OTHER INFORMATION: Primer

<400> SEQUENCE: 92
agagtctgcg gaaaacctca                                              20

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
ccttgagctc atacccatc                                               20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
actaaagccg cagagcagag                                              20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
gagaggcctc gtcctgtgta                                              20

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
tcccactcac atttcccaat                                              20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
caagggcatg aggagtgttt                                              20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
```
actccatgat tgcacaacga                                               20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
tcattccacc agcaatgtgt                                               20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
ggccactgca gaagaaagag                                               20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
ctgttgtccc agccctgtat                                               20

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
aggtgagtcc aggctagcaa                                               20

<210> SEQ ID NO 103
<211> LENGTH: 20
<212> TYPE: DNA
<213> ORGANISM: Artificial Sequence
<220> FEATURE:
<223> OTHER INFORMATION: Primer

<400> SEQUENCE: 103
gagcccgagc ggataatact                                               20

<210> SEQ ID NO 104
<211> LENGTH: 20
<212> TYPE: DNA
<213> ORGANISM: Artificial Sequence
<220> FEATURE:
<223> OTHER INFORMATION: Primer

<400> SEQUENCE: 104
attaggaccg cacaggacac                                               20

<210> SEQ ID NO 105
<211> LENGTH: 20
<212> TYPE: DNA

```
<213> ORGANISM: Artificial Sequence
<220> FEATURE:
<223> OTHER INFORMATION: Primer

<400> SEQUENCE: 105
gcggctaggg tggtacttct                                               20

<210> SEQ ID NO 106
<211> LENGTH: 18
<212> TYPE: DNA
<213> ORGANISM: Artificial Sequence
<220> FEATURE:
<223> OTHER INFORMATION: Primeer

<400> SEQUENCE: 106
ctcgtcctcg tcctcgtc                                                 18

<210> SEQ ID NO 107
<211> LENGTH: 18
<212> TYPE: DNA
<213> ORGANISM: Artificial Sequence
<220> FEATURE:
<223> OTHER INFORMATION: Primer

<400> SEQUENCE: 107
gaggacgacg aggacgag                                                 18

<210> SEQ ID NO 108
<211> LENGTH: 20
<212> TYPE: DNA
<213> ORGANISM: Artificial Sequence
<220> FEATURE:
<223> OTHER INFORMATION: primer

<400> SEQUENCE: 108
ccactttcaa ggcctctctg                                               20

<210> SEQ ID NO 109
<211> LENGTH: 18
<212> TYPE: DNA
<213> ORGANISM: Artificial Sequence
<220> FEATURE:
<223> OTHER INFORMATION: Primer

<400> SEQUENCE: 109
gaggacgacg aggacgag                                                 18

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
ccactttcaa ggcctctctg                                               20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
ctggggtgac tctagcaagg                                               20
```

```
<210> SEQ ID NO 112
<211> LENGTH: 20
<212> TYPE: DNA
<213> ORGANISM: Artificial Sequence
<220> FEATURE:
<223> OTHER INFORMATION: Primer

<400> SEQUENCE: 112
tcacaccaag gcaaatttca                                                  20

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
cccccaaagg gaactatttt                                                  20

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
gaactgaggt ggtggcattt                                                  20

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
ttcagggtct gggaatatgg                                                  20

<210> SEQ ID NO 116
<211> LENGTH: 20
<212> TYPE: DNA
<213> ORGANISM: Artificial Sequence
<220> FEATURE:
<223> OTHER INFORMATION: Primer

<400> SEQUENCE: 116
tccaacttgt ttggctacga                                                  20

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
ggcccctaag aaacacagag                                                  20

<210> SEQ ID NO 118
<211> LENGTH: 20
<212> TYPE: DNA
<213> ORGANISM: Artificial Sequence
<220> FEATURE:
```

<223> OTHER INFORMATION: Primer

<400> SEQUENCE: 118
cctgtagacc ccagagacca                                              20

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
ggtccaaatt gtagggctga                                              20

<210> SEQ ID NO 120
<211> LENGTH: 20
<212> TYPE: DNA
<213> ORGANISM: Artificial Sequence
<220> FEATURE:
<223> OTHER INFORMATION: Primeer

<400> SEQUENCE: 120
ttccccagga ggttctcttt                                              20

<210> SEQ ID NO 121
<211> LENGTH: 20
<212> TYPE: DNA
<213> ORGANISM: Artificial Sequence
<220> FEATURE:
<223> OTHER INFORMATION: Primer

<400> SEQUENCE: 121
ccagatcaag gggaatgcta                                              20

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
caaggcagac caatccattt                                              20

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
caaagtaagc atccccagga                                              20

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
gcagcacctc tttcctcatc                                              20

```
<210> SEQ ID NO 125
<211> LENGTH: 20
<212> TYPE: DNA
<213> ORGANISM: Artificial Sequence
<220> FEATURE:
<223> OTHER INFORMATION: Primer

<400> SEQUENCE: 125
tggaattttt gggctgtttc                                              20

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
tttctccagg gaatttgtgc                                              20

<210> SEQ ID NO 127
<211> LENGTH: 20
<212> TYPE: DNA
<213> ORGANISM: Artificial Sequence
<220> FEATURE:
<223> OTHER INFORMATION: Primer

<400> SEQUENCE: 127
gctgctggag accagaaaag                                              20

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
cgaagggcac ctattcaaaa                                              20

<210> SEQ ID NO 129
<211> LENGTH: 33
<212> TYPE: DNA
<213> ORGANISM: Equus caballus
<220> FEATURE:
<221> NAME/KEY: CDS
<222> LOCATION: (1)..(33)

<400> SEQUENCE: 129 gcc gcc gac cga act tcg gca gag ccc gag agc                        33
Ala Ala Asp Arg Thr Ser Ala Glu Pro Glu Ser
1               5                   10

<210> SEQ ID NO 130
<211> LENGTH: 11
<212> TYPE: PRT
<213> ORGANISM: Equus caballus

<400> SEQUENCE: 130

Ala Ala Asp Arg Thr Ser Ala Glu Pro Glu Ser
1               5                   10

<210> SEQ ID NO 131
<211> LENGTH: 33
<212> TYPE: DNA
<213> ORGANISM: Equus caballus
<220> FEATURE:
```

```
<221> NAME/KEY: CDS
<222> LOCATION: (1)..(18)

<400> SEQUENCE: 131 gcc gcc gac cga act tag gcagagcccg agagc                              33
Ala Ala Asp Arg Thr
1               5

<210> SEQ ID NO 132
<211> LENGTH: 5
<212> TYPE: PRT
<213> ORGANISM: Equus caballus

<400> SEQUENCE: 132

Ala Ala Asp Arg Thr
1               5

<210> SEQ ID NO 133
<211> LENGTH: 83
<212> TYPE: PRT
<213> ORGANISM: Bos taurus

<400> SEQUENCE: 133

Ala Asn Arg Pro Pro Leu Glu Val Leu Lys Lys Ile Phe Pro His Gln
1               5                  10                  15

Lys Pro Ala Val Leu Glu Leu Ile Leu Lys Gly Cys Gly Gly Asp Leu
                20                  25                  30

Val Ser Ala Val Glu Val Leu Ser Ser Arg Ser Ser Ser Ser Ser Ala
            35                  40                  45

Ala Asp Arg Thr Ser Ala Glu Pro Glu Gly Leu Val Leu Pro Ser Asn
        50                  55                  60

Gly His Leu Phe Glu His Thr Leu Ser Ser Tyr Pro Leu Ser Ser Ser
65                  70                  75                  80

Lys Trp Ser

<210> SEQ ID NO 134
<211> LENGTH: 83
<212> TYPE: PRT
<213> ORGANISM: Equus caballus

<400> SEQUENCE: 134

Ala Asn Arg Pro Pro Leu Glu Val Leu Lys Lys Ile Phe Pro Asn Gln
1               5                  10                  15

Lys Pro Thr Val Leu Glu Leu Ile Leu Lys Gly Cys Gly Gly Asp Leu
                20                  25                  30

Val Ser Ala Val Glu Val Leu Leu Ser Ser Arg Ser Ser Ala Ser Ala
            35                  40                  45

Ala Asp Arg Thr Ser Ala Glu Pro Glu Ser Leu Val Leu Pro Ser Asn
        50                  55                  60

Gly His Thr Phe Glu His Thr Leu Ser Ser Tyr Pro Thr Ser Ser Ser
65                  70                  75                  80

Lys Trp Ser

<210> SEQ ID NO 135
<211> LENGTH: 83
<212> TYPE: PRT
<213> ORGANISM: Equus caballus
<220> FEATURE:
<221> NAME/KEY: misc_feature
<222> LOCATION: (53)..(53)
<223> OTHER INFORMATION: Xaa can be any naturally occurring amino acid
```

```
<220> FEATURE:
<221> NAME/KEY: VARIANT
<222> LOCATION: (58)..(58)

<400> SEQUENCE: 135

Ala Asn Arg Pro Pro Leu Glu Val Leu Lys Lys Ile Phe Pro Asn Gln
1               5                   10                  15

Lys Pro Thr Val Leu Glu Leu Ile Leu Lys Gly Cys Gly Gly Asp Leu
            20                  25                  30

Val Ser Ala Val Glu Val Leu Ser Ser Arg Ser Ser Ala Ser Ala
        35                  40                  45

Ala Asp Arg Thr Xaa Ala Glu Pro Glu Ser Leu Val Leu Pro Ser Asn
    50                  55                  60

Gly His Thr Phe Glu His Thr Leu Ser Ser Tyr Pro Thr Ser Ser Ser
65                  70                  75                  80

Lys Trp Ser

<210> SEQ ID NO 136
<211> LENGTH: 83
<212> TYPE: PRT
<213> ORGANISM: Homo sapiens

<400> SEQUENCE: 136

Ala Asn Arg Pro Pro Leu Glu Val Leu Lys Lys Ile Phe Pro Asn Gln
1               5                   10                  15

Lys Pro Thr Val Leu Glu Leu Ile Leu Lys Gly Cys Gly Gly Asp Leu
            20                  25                  30

Val Ser Ala Val Glu Val Leu Ser Ser Arg Ser Ser Val Thr Gly
        35                  40                  45

Ala Glu Arg Thr Ser Ala Glu Pro Glu Ser Leu Ala Leu Pro Ser Asn
    50                  55                  60

Gly His Ile Phe Glu His Thr Leu Ser Ser Tyr Pro Ile Ser Ser Ser
65                  70                  75                  80

Lys Trp Ser

<210> SEQ ID NO 137
<211> LENGTH: 83
<212> TYPE: PRT
<213> ORGANISM: Pan troglodytes

<400> SEQUENCE: 137

Ala Asn Arg Pro Pro Leu Glu Val Leu Lys Lys Ile Phe Pro Ser Gln
1               5                   10                  15

Lys Pro Thr Val Leu Glu Leu Ile Leu Gln Gly Cys Gly Gly Asp Leu
            20                  25                  30

Val Gly Ala Val Glu Val Leu Ser Ser Arg Cys Ser Val Thr Gly
        35                  40                  45

Ala Glu Arg Ser Cys Ala Glu Pro Glu Ser Leu Leu Leu Pro Pro Arg
    50                  55                  60

Gly His Ile Phe Glu His Thr Leu Ser Ser Tyr Pro Ile Ser Ser Ser
65                  70                  75                  80

Lys Trp Ser

<210> SEQ ID NO 138
<211> LENGTH: 84
<212> TYPE: PRT
<213> ORGANISM: Canis familiaris
```

```
<400> SEQUENCE: 138

Ala Asn Arg Pro Pro Leu Glu Val Leu Lys Lys Ile Phe Pro Gly Gln
1               5                   10                  15

Lys Pro Ala Val Leu Glu Leu Ile Leu Lys Gly Cys Gly Gly Asp Leu
            20                  25                  30

Val Gly Ala Val Glu Val Leu Ser Ser Arg Ser Ser Ala Ala Ala
        35                  40                  45

Ala Ser Glu Arg Thr Ala Ala Glu Pro Glu Ala Leu Val Leu Pro Pro
    50                  55                  60

Asn Gly His Leu Phe Glu His Gly Leu Gly Ser Tyr Pro Leu Ser Ser
65                  70                  75                  80

Ser Lys Trp Ser

<210> SEQ ID NO 139
<211> LENGTH: 81
<212> TYPE: PRT
<213> ORGANISM: Mus musculus

<400> SEQUENCE: 139

Ala Asn Arg Pro Pro Leu Glu Val Leu Lys Lys Ile Phe Pro Asn Gln
1               5                   10                  15

Lys Pro Thr Val Leu Glu Leu Ile Leu Lys Gly Cys Gly Gly Asp Leu
            20                  25                  30

Val Ser Ala Val Glu Val Leu Ser Ser Arg Ser Ser Ala Ala Gly
        35                  40                  45

Thr Glu Arg Thr Ala Glu Ser Leu Val Leu Pro Ser Ser Gly His
    50                  55                  60

Ile Phe Glu His Thr Leu Gly Ser Tyr Pro Ile Ser Ser Ser Lys Trp
65                  70                  75                  80

Ser

<210> SEQ ID NO 140
<211> LENGTH: 81
<212> TYPE: PRT
<213> ORGANISM: Rattus norvegicus

<400> SEQUENCE: 140

Ala Asn Arg Pro Pro Leu Glu Val Leu Lys Lys Ile Phe Pro Asn Gln
1               5                   10                  15

Lys Pro Thr Val Leu Glu Leu Ile Leu Lys Gly Cys Gly Gly Asp Leu
            20                  25                  30

Val Ser Ala Val Glu Val Leu Ser Ser Arg Ser Ser Ala Ala Gly
        35                  40                  45

Ala Glu Arg Thr Ala Glu Ser Leu Val Leu Pro Ser Ser Gly His
    50                  55                  60

Ile Phe Glu His Thr Leu Gly Ser Tyr Pro Ile Ser Ser Ser Lys Trp
65                  70                  75                  80

Ser

<210> SEQ ID NO 141
<211> LENGTH: 82
<212> TYPE: PRT
<213> ORGANISM: Gallus gallus

<400> SEQUENCE: 141

Ala Asn Arg Pro Pro Leu Glu Val Leu Lys Lys Ile Phe Pro Asn Gln
1               5                   10                  15
```

```
Lys Pro Thr Val Leu Glu Leu Ile Leu Lys Gly Cys Gly Gly Asp Leu
            20                  25              30

Val Gly Ala Val Glu Val Leu Leu Ser Ser Arg Ser Ser Val Ala Gly
        35                  40              45

Gly Glu Arg Thr Ser Glu Ser Asp Gly Leu Val Leu Pro Ser Asn Gly
    50                  55                  60

His Ile Phe Glu His Thr Leu Ser Ser Tyr Pro Ile Ser Ser Ser Lys
65                  70                  75                  80

Trp Ser

<210> SEQ ID NO 142
<211> LENGTH: 83
<212> TYPE: PRT
<213> ORGANISM: Danio rerio

<400> SEQUENCE: 142

Ala Asn Arg Pro Pro Leu Glu Val Leu Lys Lys Ile Phe Pro Ala His
1               5                   10                  15

Lys Pro Ala Val Leu Glu Leu Ile Leu Lys Gly Cys Gly Gly Asp Leu
            20                  25                  30

Val Gly Ala Ile Glu Ile Leu Leu Ser Ser Arg Ser Thr Met Lys Pro
        35                  40                  45

Glu Lys Ile Leu Ser Glu Ser Ser Asp Ala Leu Val Leu Pro Ser Asn
    50                  55                  60

Gly His Leu Phe Glu His Pro Leu Ser Ser Tyr Pro Val Ser Ser Ser
65                  70                  75                  80

Lys Trp Ser
```

METHOD TO PREDICT THE PATTERN OF LOCOMOTION IN HORSES

FIELD OF INVENTION

The present invention relates to methods for predicting the pattern of locomotion in horses including the ability of a horse to use different gaits and the ability to trot or pace at a fast speed. The methods comprise determining in a sample of DNA obtained from a horse the allele of at least one genetic marker, wherein said at least one genetic marker is located on horse chromosome 23, said marker being associated with the ability to use different gaits.

BACKGROUND

Horses show a considerable variation in their pattern of locomotion both within and between breeds. The three basic gaits in horses are walk, trot and gallop. The horses use these different gaits according to their speed, walk is used at slow speed, trot is a faster mode of locomotion and gallop is the gait horses normally use to run fast. However, some horses have the ability to also use alternative gaits, for example pace and toelt, and such horses are called gaited horses. A horse that pace moves the two legs on the same side in a lateral movement in contrast to a trotting horse that makes a diagonal movement where the diagonal front and hind legs move forward and backwards together. Furthermore, Icelandic horses are able to perform a fifth gait named toelt, which is a four beet gait with the same foot fall pattern as the walk. A characteristic feature of toelt is that the horse then always has at least one hoof touching the ground, giving a very smooth gait. Examples of other similar alternative gaits, also known as ambling gaits, are fox trot, the rack, running walk and paso cort. The alternative gaits vary in footfall pattern, timing, and cadence, and can be generally divided into four categories: pace, regular rhythm ambling, lateral ambling and diagonal ambling. Table 1 provides a classification of breeds as gaited or non-gaited horses. Most horse breeds are in fact non-gaited and only representative examples of such breeds are listed in the table. Horses representing breeds classified as non-gaited never or rarely are able to perform the alternative gaits whereas most or all horses from the gaited breeds can perform alternative gaits. There are more gaited breeds worldwide in addition to the ones listed in table 1. Sometimes, there is a considerable variation also within breeds as regards the pattern of locomotion. For instance, Icelandic horses are classified as four-gaited or five-gaited, where the former can perform walk, trot, gallop and toelt whereas the latter can also pace.

The Standardbred horse, used for harness racing has a unique ability to trot or pace at a very fast speed without falling into gallop which is the normal gait at high speed for a horse. In North America, a subpopulation of Standardbred horses that pace at very high speed has been developed. Other horse breeds used for harness racing includes breeds like the Cold-blooded trotter, Finnhorses, the Frensch trotter and the Orlove trotter.

The pattern of locomotion in horses is under strong selection in horse breeding. For instance, the ability to race using gallop, trot and pace are selected in Thoroughbred horses, Standardbred trotters and Standardbred pacers, respectively. Horses with the ability to use alternative gaits are also highly desired by some riders and is a trait upon which many specialized breeds have been developed. Methods for predicting the pattern of locomotion in a horse, i.e. its ability to use different gaits, would therefore have a great utility in the horse breeding industry.

BRIEF DESCRIPTION OF INVENTION

The present inventors have identified a genetic locus in horses that determines the horse's ability to use different gaits and the ability to trot at a fast speed. A premature stop codon in the gene for the doublesex and mab-3 related transcription factor 3 (DMRT3) was found in all tested horses with the ability to perform alternative gaits. Mutant horses express a truncated DMRT3 protein which lacks the last 174 amino acid residues but maintains a functional DNA-binding domain. DMRT3 is expressed in a subset of neurons in the spinal cord of the horse.

Accordingly the present invention provides methods for predicting the pattern of locomotion in horses including the ability of a horse to use different gaits, the ability to trot or pace at a fast speed, and the ability to perform in dressage.

A first aspect of the invention provides methods for predicting the pattern of locomotion in horses including the ability of a horse to use alternative gaits, the ability to trot at a fast speed, and the ability to perform in dressage which comprise extracting protein from a sample obtained from a horse. The methods further comprise determining in said protein sample the presence or absence of a truncated form of the DMRT3 protein. The DMRT3 protein can be a DMRT3 protein truncated at amino acid position 300 corresponding to the protein SEQ ID NO: 4. The determination can be made by use of an immunochemical method, such as Western blot, using an anti DMRT3 antibody.

A second aspect of the invention provides methods for predicting the pattern of locomotion in horses including the ability of a horse to use alternative gaits, the ability to trot at a fast speed, and the ability to perform in dressage which comprise extracting DNA from a sample obtained from a horse. The methods further comprise determining in said DNA the allele of at least one genetic marker, wherein said at least one genetic marker is located in the region between the flanking SNPs at nucleotide positions 22,628,976 (corresponding to position 51 in SEQ ID NO: 6) and 23,315,071 (corresponding to position 51 in SEQ ID NO: 7) on horse chromosome 23.

The genetic marker can be selected from single nucleotide polymorphisms (SNPs) and insertion/deletions (INDELs).

Preferably, the genetic marker is selected from the genetic markers listed in Tables 4, 5, 7 and 8.

Preferably the genetic marker is located in the region between the flanking SNPs at nucleotide positions 22,919,878 and 23,011,289 on horse chromosome 23.

Preferably, the genetic marker is selected from the genetic markers listed in Table 8.

Most preferably the genetic marker is located at position 22,999,655 on horse chromosome 23, corresponding to position 939 in SEQ ID NO:1.

More specifically, the methods can comprise identifying in said DNA the nucleotide in one or more specific position(s) selected from the positions 22,919,878; 22,920,361; 22,920,434; 22,920,646; 22,920,717; 22,921,203; 22,922,079; 22,922,780; 22,923,569; 22,924,120; 22,924,142; 22,924,299; 22,924,380; 22,924,407; 22,926,098; 22,926,188; 22,926,872; 22,927,387; 22,927,607; 22,928,220; 22,928,537; 22,928,587; 22,929,137; 22,930,011; 22,932,024; 22,932,895; 22,933,218; 22,936,034; 22,940,759; 22,942,423; 22,945,643; 22,946,599; 22,948,774; 22,949,055; 22,949,108; 22,949,240; 22,949,710; 22,956,846; 22,960,132; 22,960,528; 22,960,710; 22,964,042;

22,965,059; 22,967,119; 22,967,656; 22,967,915; 22,968,898; 22,973,984; 22,974,589; 22,979,124; 22,980,014; 22,982,879; 22,984,588; 22,985,746; 22,988,210; 22,988,991; 22,993,092; 22,994,591; 22,999,058; 22,999,655; 23,002,606; 23,003,956; 23,008,772; 23,008,789; 23,009,648; 23,010,164; and 23,011,289, on horse chromosome 23.

Most preferably the methods comprise identifying in said DNA the nucleotide in the specific position 22,999,655 on horse chromosome 23.

More specifically, the methods can comprise determining in said DNA the presence or absence of:
i) the nucleotide C in a nucleotide position corresponding to position 939 in SEQ ID NO: 1,
ii) the nucleotide A in a nucleotide position corresponding to position 939 in SEQ ID NO: 3,
iii) the nucleotide C and/or T in a nucleotide position corresponding to position 51 in SEQ ID NO: 5,
iv) the nucleotide A and/or G in a nucleotide position corresponding to position 51 in SEQ ID NO: 6,
v) the nucleotide C and/or T in a nucleotide position corresponding to position 51 in SEQ ID NO: 7,
vi) the nucleotide G and/or C in a nucleotide position corresponding to position 51 in SEQ ID NO: 8,
vii) the nucleotide A and/or G in a nucleotide position corresponding to position 51 in SEQ ID NO: 9,
viii) the nucleotide T and/or G in a nucleotide position corresponding to position 51 in SEQ ID NO: 10,
ix) the nucleotide T and/or C in a nucleotide position corresponding to position 51 in SEQ ID NO: 11,
x) the nucleotide C and/or T in a nucleotide position corresponding to position 51 in SEQ ID NO: 12,
xi) the nucleotide A and/or G in a nucleotide position corresponding to position 51 in SEQ ID NO: 13,
xii) the nucleotide A and/or C in a nucleotide position corresponding to position 51 in SEQ ID NO: 14
xiii) the nucleotide G and/or C in a nucleotide position corresponding to position 51 in SEQ ID NO: 15,
xiv) the nucleotide C and/or T in a nucleotide position corresponding to position 51 in SEQ ID NO: 16,
xv) the nucleotide G and/or A in a nucleotide position corresponding to position 51 in SEQ ID NO: 17,
xvi) the nucleotide G and/or C in a nucleotide position corresponding to position 51 in SEQ ID NO: 18,
xvii) the nucleotide C and/or A in a nucleotide position corresponding to position 51 in SEQ ID NO: 19,
xviii) the nucleotide T and/or C in a nucleotide position corresponding to position 51 in SEQ ID NO: 20,
xix) the nucleotide C and/or T in a nucleotide position corresponding to position 51 in SEQ ID NO: 21,
xx) the nucleotide C and/or T in a nucleotide position corresponding to position 51 in SEQ ID NO: 22,
xxi) the nucleotide C and/or A in a nucleotide position corresponding to position 51 in SEQ ID NO: 23,
xxii) the nucleotide C and/or G in a nucleotide position corresponding to position 51 in SEQ ID NO: 24,
xxiii) the nucleotide A and/or T in a nucleotide position corresponding to position 51 in SEQ ID NO: 25, Preferably the methods comprise determining in said DNA the presence or absence of:
i) the nucleotide C in a nucleotide position corresponding to position 939 in SEQ ID NO: 1,
ii) the nucleotide A in a nucleotide position corresponding to position 939 in SEQ ID NO: 3,
iii) the nucleotide C and/or T in a nucleotide position corresponding to position 51 in SEQ ID NO: 5,
iv) the nucleotide C and/or T in a nucleotide position corresponding to position 51 in SEQ ID NO: 7,
v) the nucleotide T and/or C in a nucleotide position corresponding to position 51 in SEQ ID NO: 20,
vi) the nucleotide C and/or T in a nucleotide position corresponding to position 51 in SEQ ID NO: 21,
vii) the nucleotide C and/or T in a nucleotide position corresponding to position 51 in SEQ ID NO: 22,
viii) the nucleotide C and/or A in a nucleotide position corresponding to position 51 in SEQ ID NO: 23,
ix) the nucleotide C and/or G in a nucleotide position corresponding to position 51 in SEQ ID NO: 24,
x) the nucleotide A and/or T in a nucleotide position corresponding to position 51 in SEQ ID NO: 25, Most preferably the methods comprise determining in said DNA the presence or absence of:
i) the nucleotide C in a nucleotide position corresponding to position 939 in SEQ ID NO: 1. or
ii) the nucleotide A in a nucleotide position corresponding to position 939 in SEQ ID NO: 3.

The horse can be selected from any horse or breed of horses belonging to the species *Equus caballus*. Examples of horse breeds can be found in Table 1.

TABLE 1

Classification of horse breeds as gaited or non-gaited, where gaited horses have the ability to perform alternative gaits in addition to the three basic gaits walk, trot and gallop.

| Breed | Classification |
| --- | --- |
| American Saddlebred | gaited |
| Campolina | gaited |
| Icelandic horse | gaited |
| Kentucky Mountain Saddle Horse | gaited |
| Mangalarga Marchador | gaited |
| Marwari horse | gaited |
| Missouri Foxtrotter | gaited |
| Paso Fino | gaited |
| Peruvian Paso | gaited |
| Racking horse | gaited |
| Rocky Mountain Horse | gaited |
| Spotted Saddle horse | gaited |
| Standardbred* | gaited |
| Tennessee Walker | gaited |
| Walkaloosa | gaited |
| Akhal teke | non-gaited |
| American Paint Horse | non-gaited |
| Andalusian | non-gaited |
| Arabian | non-gaited |
| Belgian | non-gaited |
| Dole | non-gaited |
| Exmoor Pony | non-gaited |
| Friesian | non-gaited |
| Haflinger | non-gaited |
| Hanoverian | non-gaited |
| Lusitano | non-gaited |
| North Swedish Draft horse | non-gaited |
| Norwegian Fjord | non-gaited |
| Quarter Horse | non-gaited |
| Selle Francais | non-gaited |
| Shetland Pony | non-gaited |
| Suffolk Punch | non-gaited |
| Thoroughbred | non-gaited |
| Trakehner | non-gaited |

*Two separate populations, pacers and trotters, many trotters seem to be able to toelt.

According to one aspect of the invention the methods according to the present invention can be used for paternity testing of horses.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

LEGENDS TO FIGURES

The following drawings form part of the present specification and are included to further demonstrate certain aspects of the present invention. The invention may be better understood by reference to one or more of these drawings in combination with the detailed description of specific embodiments presented herein.

FIG. 1. Results of genome-wide analysis of 70 Icelandic horses classified as four-gaited or five-gaited. The highly associated SNP at nucleotide position Chr23:22,967,656 base pairs is marked by an arrow.

Figure 2:

FIG. 2. Genomic region harboring the Gait locus on chromosome 23 controlling the pattern of locomotion in horses. The DMRT3 gene is not properly annotated in this assembly but it is represented by the Ensembl transcript ENSECAT00000025062 indicated by an arrow in this figure. The figure is adapted from an output from the UCSC genome browser (www.genome.ucsc.edu).

FIG. 3. Nucleotide and amino acid alignment for codon 296 to 306 of horse DMRT3 including codon 301 in which a nonsense mutation occurs in the allele associated with the ability to pace.

Figure 4:
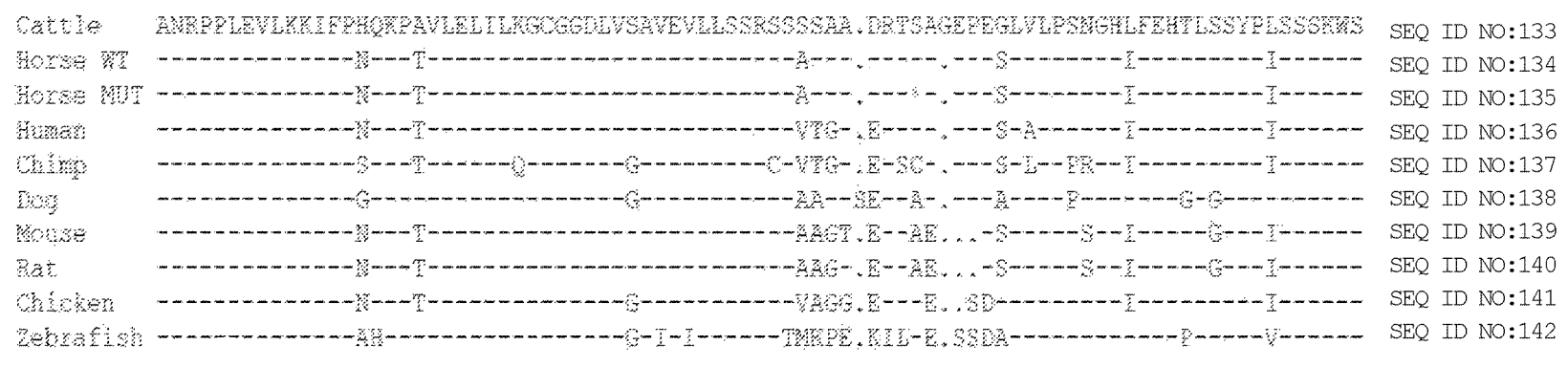

FIG. 4. Alignment of amino acids 249 to 331 (numbered according to the horse sequence) in the DMRT3 protein from different vertebrate species including the wild-type (WT) and mutant (MUT) form of the horse DRMT3 protein. "." indicates gap in the alignment; "-" indicates identity to the master sequence used (cattle); * indicates the nonsense mutation at codon 301 in the horse mutant allele.

Figure 5:
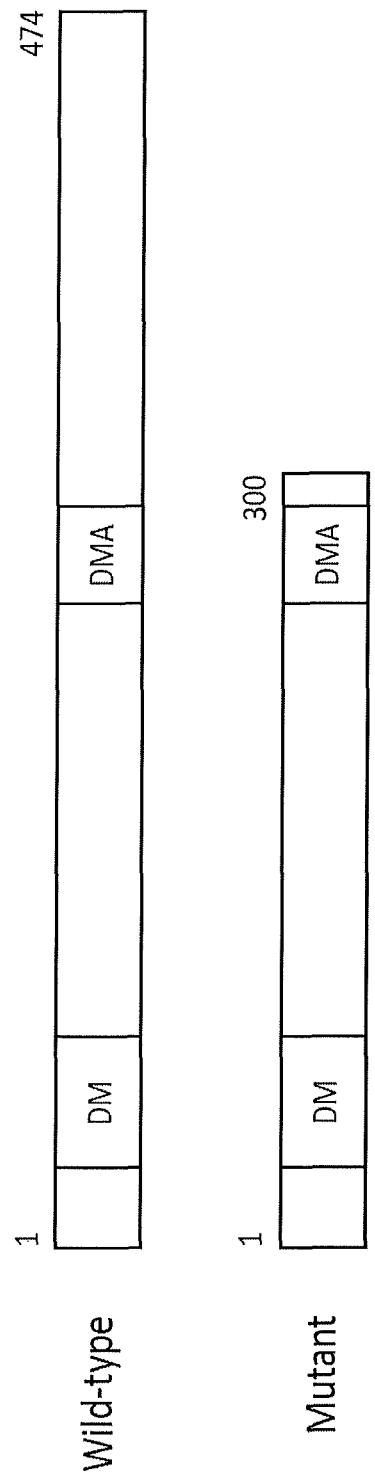

FIG. 5. Schematic presentation of the predicted wild-type and mutant (gait) forms of the DMRT3 protein in horses. DM=zinc-finger like DNA binding module. DMA=protein domain of unknown function present in DMRT proteins.

Figure 6:
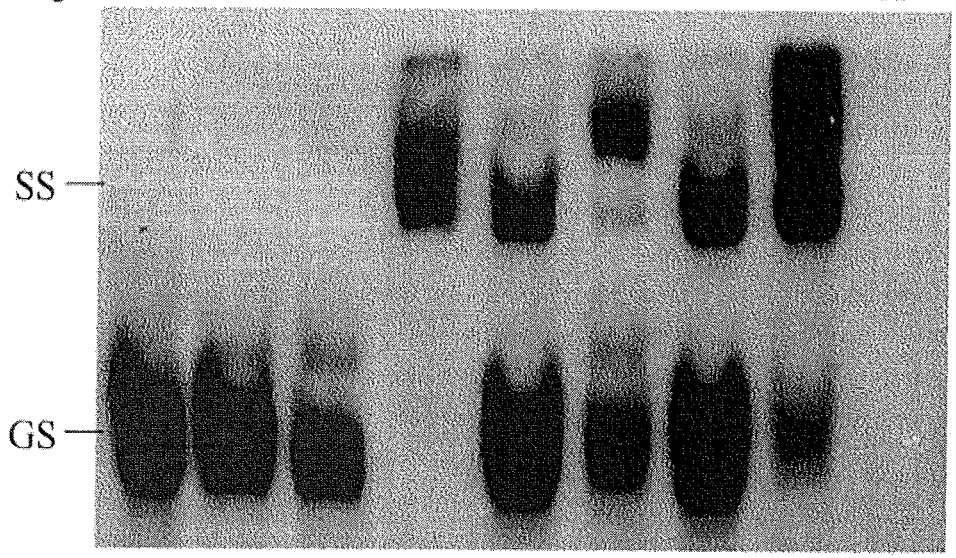

FIG. 6. EMSA using an oligonucleotide representing a DMRT3-binding motif and in vitro-translated myc-tagged DMRT3 wild-type and mutant proteins.

Super-shifts were demonstrated using an anti-myc antibody (that recognizes both forms) or with an anti-DMRT3 antibody that recognizes the C-terminal part of the wild-type protein, but not the truncated form. An oligonucleotide corresponding to a DMRT1—binding site was also used and gave similar results (data not shown). The cold competing oligonucleotide was added in 150× excess. GS=gel-shift representing complex between DMRT3 protein and oligonucleotide; SS=super-shift representing complex between antibody, DMRT3 protein and oligonucleotide.

DETAILED DESCRIPTION OF THE INVENTION

The present inventors have demonstrated that there is a locus, here named Gait, on horse chromosome 23 that has a major impact on the pattern of locomotion in horses. The present results show that homozygosity for a recessive allele at this locus is required for the ability of a horse to pace. It is postulated that the nonsense mutation at nucleotide position 22,999,655 in exon 2 of the DMRT3 gene is the causative mutation for the Gait allele. DMRT3 is a highly conserved gene present in all vertebrates studied so far. The function of the DMRT3 protein has not been established by any previous studies but the fact that it is expressed in brain and in the spinal cord of the mouse (MGI, www.informaticsjax.org) is consistent with a critical role for controlling locomotion as demonstrated by the present study. The nonsense mutation underlying the gait allele may very well have a phenotypic effect in the heterozygous condition since it occurs in the last exon of DMRT3 and is expected to encode a truncated form of the protein (SEQ ID NO:4) that lacks the last 174 amino acids (FIG. 5). The DNA binding DM domain of DMRT3 is located in the N-terminal part that is maintained in the truncated form (FIG. 5). The mutant form of DMRT3 may therefore be able to bind to its target DNA sequences but may show defects as regards the interaction with other proteins required for its normal function and may therefore has a dominant-negative effect in heterozygotes. It is worth noticing that only one of the Icelandic horses was homozygous for the wild-type (non-pace) allele at the Gait locus.

This study has established a genetic marker that can be used to predict the genetic constitution of a horse as regards its pattern of locomotion. We predict that the gait allele is present in most, if not all, gaited breeds some of which are listed as gaited in Table 1 and it may occur at a low frequency in other breeds as well. The marker also predictes a horse capacity to trot or pace at a high speed as it is found at a high frequency in horses used for harness racing. Further, we predict that horses with atleast one wild-type allel are better at showjumping, traditional dressage, and completion racing in gallop.

The pattern of locomotion determines the ability of a horse to use alternative gaits, as well as the horse's ability to trot or pace at a fast speed, and its ability to performe in dressage. Alternative gaits include, pace, and the ambling gaits exemplified by toelt, running walk, rack, classic fino, paso corto, paso largo, paso ilano, sobreandando, fox trot.

A horse being homozygous or heterozygous for the gait allele can be predicted to have the ability to use alternative gaits and to trot at high speed. A horse being homozygous or heterozygote for the wild type allele can be predicted to have better ability to perform in showjumping, dressage, and completion racing in gallop.

The utility of this invention in the horse breeding industry includes the determination of the genotype of potential breeding animals to maximise the chance to obtain a progeny with a favoured pattern of locomotion. The information about the genotype at the DMRT3 locus may also be used by sellers and buyers of horses to predict the ability of the horse to perform different gaits. Furthermore, the methods according to the invention can be used to effectively introgress the gait allele into non-gaited breeds.

According to one aspect of the invention the methods according to the present invention can be used for selecting horses for breeding.

Accordingly, one aspect of the invention provides methods for selecting a horse for breeding, said methods comprising determining in a DNA sample obtained from said horse the allele of at least one genetic marker, wherein said at least one genetic marker is located in the region between the flanking SNPs at nucleotide positions 22,628,976 on horse chromosome 23. The genetic marker can be selected from single nucleotide polymorphisms (SNPs) and insertion/deletions (INDELs).

Preferably, the genetic marker is selected from the genetic markers listed in Tables 4, 5, 7 and 8.

Preferably the genetic marker is located in the region between the flanking SNPs at nucleotide positions 22,919,878 and 23,011,289 on horse chromosome 23.

Preferably, the genetic marker is selected from the genetic markers listed in Table 8.

Most preferably the genetic marker is located at position 22,999,655 on horse chromosome 23, corresponding to position 939 in SEQ ID NO:1.

The most reliable test for determining the genotype at the *Gait locus* is to determine the presence and/or absence of the nonsense mutation in exon 2 of DMRT3 (nucleotide position 22,999,655 on chromosome 23, corresponding to nucleotide position 939 in SEQ ID NO:3). However, genetic markers located in the interval between the flanking markers at nucleotide positions 22,628,976 and 23,315,071, and more specifically genetic markers located in the interval between positions 22,919,878 and 23,011,289, exemplified by the markers listed in Table 8, show a more or less strong association to the genotype of the causative SNP at nucleotide position 22,999,655 due to the presence of linkage disequilibrium in the region. Accordingly, one or more of these markers, individually or in combination, can be used to determine the genotype at the *Gait locus*, and can consequently as well be used in the methods according to the present invention.

The term "sample" or "biological sample" according to the present invention refers to any material containing nucleated cells from said horse to be tested. In a preferred embodiment the biological sample to be used in the methods of the present invention is selected from the group consisting of blood, sperm, hair roots, milk, body fluids as well as tissues including nucleated cells.

DNA extraction, isolation and purification methods are well-known in the art and can be applied in the present invention. Standard protocols for the isolation of genomic DNA are inter alia referred to in Sambrook, J., Russell. D. W. Molecular Cloning: A Laboratory Manual, the third edition, Cold Spring Harbor Laboratory Press, Cold Spring Harbor. New York, 1.31-1.38, 2001 and Sharma. R. C., et al. "A rapid procedure for isolation of RNA-free genomic DNA from mammalian cells", BioTechniques, 14. 176-178. 1993.

According to the present invention the term "SNP" refers to a single nucleotide polymorphism at a particular position in the horse genome that varies among a population of individuals. SNPs can be identified by their location within the disclosed particular sequence, i.e. within the interval of 22,628,976 and 23,315,071 base pairs on horse chromosome 23 or their name as shown in Tables 4, 5, 7 and 8. SNPs identified as being useful for predicting the ability of a horse to use different gaits according to the present invention are shown in Tables 4, 5, 7 and 8. For example, the SNP BIEC2-620109 of Table 5 indicates that the nucleotide base (or the allele) at nucleotide position 22,967,656 on chromosome 23 of the reference sequence as referred to herein may be either Cytosine (C) or Thymidine (T). The allele associated with or indicative for a horse able to use five gaits is in the case of SNP BIEC2-620109 of Table 5 Thymidine (T).

The term "determining in said DNA the allele of at least one genetic marker" in accordance with the present invention refers to a method for determining or identifying whether a particular nucleotide sequence is present in a DNA sample.

The term "identifying in said DNA the nucleotide in one or more specific position on the horse chromosome 23" refers to a method for determining the identity of the nucleotide in said specific position on the horse chromosome 23, i.e. to determine whether the nucleotide in said specific position is Adenosine (A), Cytosine (C), Guanosine (G), or Thymidine (T).

There are several methods known by those skilled in the art for determining whether a particular nucleotide sequence is present in a DNA sample and for identifying the nucleotide in a specific position in a DNA sequence. These include the amplification of a DNA segment encompassing the genetic marker by means of the polymerase chain reaction (PCR) or any other amplification method, interrogate the genetic marker by means of allele specific hybridization, the 3'exonuclease assay (Taqman assay), fluorescent dye and quenching agent-based PCR assay, the use of allele-specific restriction enzymes (RFLP-based techniques), direct sequencing, the oligonucleotide ligation assay (OLA), pyrosequencing, the invader assay, minisequencing, DHPLC-based techniques, single strand conformational polymorphism (SSCP), allele-specific PCR, denaturating gradient gel electrophoresis (DGGE), temperature gradient gel electrophoresis (TGGE), chemical mismatch cleavage (CMC), heteroduplex analysis based system, techniques based on mass spectroscopy, invasive cleavage assay, polymorphism ratio sequencing (PRS), microarrays, a rolling circle extension assay, HPLC-based techniques, extension based assays, ARMS (Amplification Refractory Mutation System), ALEX (Amplification Refractory Mutation Linear Extension), SBCE (Single base chain extension), molecular beacon assays, invader (Third wave technologies), ligase chain reaction assays, 5'-nuclease assay-based techniques, hybridization capillary array electrophoresis (CAE), protein truncation assays (PTT), immunoassays, and solid phase hybridization (dot blot, reverse dot blot, chips). This list of methods is not meant to be exclusive, but just to illustrate the diversity of available methods. Some of these methods can be performed in accordance with the methods of the present invention in microarray format (microchips) or on beads.

The invention thus also relates to the use of primers or primer pairs, wherein the primers or primer pairs hybridize(s) under stringent conditions to the DNA comprising the interval between nucleotide positions 22,628,976 and 23,315,071, preferably between positions 22,919,878 and 23,011,289, base pairs on horse chromosome 23, or to the complementary strand thereof.

Preferably the primers or primer pairs hybridize(s) under stringent conditions to the sequences SEQ ID NO: 1, 3 and 5 to 25.

Preferably, the primers of the invention have a length of at least 14 nucleotides such as 17 or 21 nucleotides.

More specifically the primers can be selected from SEQ NO:26, SEQ ID NO:27, SEQ ID NO:30, and SEQ ID NO:31.

In one embodiment, the primers actually binds to the position of the SNPs as referred to in Tables 4, 5, 7 and 8. Such an allele specific oligonucleotide in accordance with the present invention is typically an oligonucleotide of at least 14 to 21 nucleotide bases in length designed to detect a difference of a single base in the target's genetic sequence of the horse to be tested. In accordance with the present invention one or more specific primers can be applied in order to identify more than a single SNP as referred to herein. As a consequence, when binding is performed under stringent conditions, such primer or such primers is/are useful to distinguish between different polymorphic variants as binding only occurs if the sequences of the primer and the target have full complementarity. It is further preferred that the primers have a maximum length of 24 nucleotides. Such primers can be coupled with an appropriate detection method such as an elongation reaction or an amplification reaction, which may be used to differentiate between the polymorphic variants and then draw conclusions with regard to the horse as regards its ability to use different gaits.

Hybridisation is preferably performed under stringent or highly stringent conditions. "Stringent or highly stringent conditions" of hybridization are well known to or can be established by the person skilled in the art according to conventional protocols. Appropriate stringent conditions for each sequence may be established on the basis of well-known parameters such as temperature, composition of the nucleic acid molecules, salt conditions etc.: see, for example, Sambrook et al. "Molecular Cloning, A Laboratory Manual", CSH Press, Cold Spring Harbor, 1989 or Higgins and Hames (eds.), "Nucleic acid hybridization, a practical approach", IRL Press, Oxford 1985, see in particular the chapter "Hybridization Strategy" by Britten & Davidson. Typical (highly stringent) conditions comprise hybridization at 65° C. in 0.5×SSC and 0.1% SDS or hybridization at 42° C. in 50% formamide, 4×SSC and 0.1% SDS. Hybridization is usually followed by washing to remove unspecific signals. Washing conditions include conditions such as 65° C., 0.2×SSC and 0.1% SDS or 2×SSC and 0.1% SDS or 0.3×SSC and 0.1% SDS at 25° C.-65° C.

The term "nucleotide positions 22,628,976 and 23,315,071 base pairs on horse chromosome 23" and other similar denoted nucleotide positions refer to the horse reference sequence according to the September 2007 *Equus caballus* draft assembly EquCab2 (UCSC version equCab2). EquCab2 was produced by The Broad Institute. EquCab2 is available at the www.genome.ucsc.edu genome browser.

EXAMPLES

A genome-wide screen for genes affecting pattern of locomotion using the horse SNP chip comprising assays for 54,602 single nucleotide polymorphisms in the horse genome (Illumina EquineSNP50 BeadChip; http://www.illumina.com/products/equine_snp50_whole_genome_genotyping_kits.ilmn) was performed. A population material comprising 70 Icelandic horses in which 30 were classified as four-gaited and 40 were classified as five-gaited, i.e. only the latter had a documented ability to pace, was used in the assay.

Animal Material.

Blood samples were collected from 70 Icelandic horses from Sweden. Genomic DNA was prepared from all horses using QIAamp DNA Blood Midi Kit (Qiagen). The owners of the horses were asked to classify their horses as four-gaited or five-gaited. Hair samples were collected from 61 Swedish Standardbred horses and 2 North-Swedish Trotter. DNA from six hair roots was extracted by adding 97 μl Chelex solution and 7 μl Proteinas K and incubated in 56° C. for 60 minutes followed by an incubation in 95° C. for 10 minutes.

Genome-Wide Analysis (GWA).

The GWA was performed using the Illumina EquineSNP50 BeadChip (http://www.illumina.com/products/equine_snp50_whole_genome_genotyping_kits.ilmn). The statistical analysis of the data was carried out using the software PLINK (Purcell et al. 2007. *PLINK: a tool set for whole genome association and population-based linkage analyses. Am. J. Hum. Genet.* 81:559-575).

DNA Sequencing.

A number of coding and non-coding regions located between the flanking SNPs at nucleotide positions 22,628,976 and 23,315,071 base pairs on horse chromosome 23 was PCR amplified and sequenced to identify sequence polymorphisms. All primers used for these experiments are listed in Table 2. The amplicons were amplified with standard PCR conditions and (2720 Thermal Cycler, Applied Biosystems, Foster City, Calif.). Standard Sanger sequencing was performed using an AB3730 capillary sequencer (Applied Biosystems, Foster City, Calif.).

TABLE 2

Primers used for PCR amplification and sequencing of selected regions in horses

| Amplicon | Amplified region Nucleotide positions | Forward primer | SEQ ID NO: | Reverse primer | SEQ ID NO: |
|---|---|---|---|---|---|
| ANKRD15exon1.1 | chr23:22792627-22793280 | TCATACCAGCTTGCCACACT | 35 | GAGGAGAGAGAGCTCGTGGA | 36 |
| ANKRD15exon1.2 | chr23:22793162-22793792 | CTAATGGAGACCCGCAGAAG | 37 | GCCGGAACTCCTTTATCCTC | 38 |
| ANKRD15exon1.3 | chr23:22793704-22794386 | GAGAAGTGGCGGGGAATTAT | 39 | GCCCCACGACTTTATTCTCA | 40 |
| ANKRD15exon1.4 | chr23:22794261-22794946 | TGCAGACGAGAGACCAAATG | 41 | AAACCCAGAAGTGCCTGAGA | 42 |
| ANKRD15exon1.5 | chr23:22794844-22795453 | GCGGACAGTGGCTATAGGAG | 43 | AATACATTGTCCCCACCCTTC | 44 |
| ANKRD15exon2 | chr23:22807940-22808575 | ATGGGATTTGAGCTGAGTGG | 45 | AAGCCTGATGCTGAGAAGGA | 46 |
| ANKRD15exon3 | chr23:22809005-22809616 | TTGCATGCACACAATTTTCC | 47 | CTGGGGGTTTCTGAGTTCTG | 48 |
| ANKRD15exon4 | chr23:22810246-22810904 | GCAACCCAGGTTATCCCTTT | 49 | TCACCTTCTGCACTTGCATT | 50 |
| ANKRD15exon5 | chr23:22812005-22812621 | AAGTCGACTGAGGGGCTCTT | 51 | ACCTTGGCCCAGATAGGTTT | 52 |
| ANKRD15exon6 | chr23:22815102-22815741 | TCCCCAGGAACATACAGCTC | 53 | TGGAAAGGATTTGAGGATGC | 54 |
| ANKRD15exon7 | chr23:22817755-22818429 | GCTTCTGGCCTCACGAAATA | 55 | TGGCATGAAGACACCACAAT | 56 |
| ANKRD15exon8 | chr23:22818653-22819254 | AGCCCCAGTACAGACCACAC | 57 | GGGAAGTCGCCTACACTGAA | 58 |
| ANKRD15exon9 | chr23:22820739-22821346 | GAGGATCCGTGGGATACAGA | 59 | AGCAAGTCTCCTGAGCAAGC | 60 |

TABLE 2-continued

Primers used for PCR amplification and sequencing of selected regions in horses

| Amplicon | Amplified region Nucleotide positions | Forward primer | SEQ ID NO: | Reverse primer | SEQ ID NO: |
|---|---|---|---|---|---|
| ANKRD15exon10 | chr23:22821626-22822233 | CAGAGGACACATCTGCCTGA | 61 | CAAAACCATCCTGGAAATGG | 62 |
| ANKRD_GAP | chr23:22836558-22837273 | GTCCATCCCCTTCTCTCCTC | 63 | TGTCAGCTGCAGAATGGAAG | 64 |
| PRIMER_DS7 | chr23:22851938-22852292 | AGACTGGCCCTGAGCTAACA | 65 | CTGAAGGTGCCCTCTACAGC | 66 |
| PRIMER_DS5 | chr23:22868140-22868803 | TTACCTGCCCCTTTGTTTTG | 67 | CATCTTTGCCCCTCAGACTC | 68 |
| PRIMER_DS2 | chr23:22869516-22870124 | TTACGTGGCACCCCTACTTC | 69 | AGCCTGGACTCTGTCCTTGA | 70 |
| PRIMER_DS1 | chr23:22872699-22873368 | TGCTGCCCTCTGTCTATGTG | 71 | AAAGTAACGATGCGGTGGAC | 72 |
| PRIMER_DS4 | chr23:22874773-22875445 | AAATGGCTGTGCCGTTTTAC | 73 | CTGTGTGACCAAGCTCTCCA | 74 |
| PRIMER_DS3 | chr23:22876084-22876784 | GAAAATGCTGACGTGCTGAA | 75 | CTTGCTGCCTTTTGCCTATC | 76 |
| PRIMER_DS6 | chr23:22876563-22877255 | GCAGAGCGACCTGGAGATAG | 77 | GGCCTTAGAGGGACACATGA | 78 |
| BIETOP-620109B_3 | chr23:22967269-22967902 | CCTCTCACCCAGACACCATT | 79 | AGTTGGCAAACAACAGGACA | 80 |
| BIETOP-620109D_2 | chr23:22967525-22968019 | AAGTCCTTTCTTGGGGGCTA | 81 | GGTCCATCGTTGACCAAAAT | 82 |
| BIETOP-620109C_2 | chr23:22967526-22968041 | AGTCCTTTCTTGGGGGCTAA | 83 | ACGGCACCACCATCATCTAT | 84 |
| DMRT3exon0 | chr23:22985884-22986463 | GCCCCAACTTAAGACCCTCT | 85 | CCGCGCTGCTTAGGAGTC | 86 |
| DMRT3exon0B | chr23:22985884-22987295 | GCCCCAACTTAAGACCCTCT | 87 | TACCTGGCTTGTCGAGCTG | 88 |
| DMRT3GAP | chr23:22986413-22987358 | GAGCACGCTCAGACCCTATC | 89 | AAAGAGCTCCGAAGTTTTGC | 90 |
| DMRT3exon2.1 | chr23:22999117-22999797 | CTCCTTCCAAGAAGCCTGTG | 91 | AGAGTCTGCGGAAAACCTCA | 92 |
| DMRT3exon2.2 | chr23:22999709-23000396 | CCTTGAGCTCATACCCCATC | 93 | ACTAAAGCCGCAGAGCAGAG | 94 |
| DMRT3exon2.3 | chr23:23000251-23001049 | GAGAGGCCTCGTCCTGTGTA | 95 | TCCCACTCACATTTCCCAAT | 96 |
| PRIMER_1 | chr23:23009567-23010210 | CAAGGGCATGAGGAGTGTTT | 97 | ACTCCATGATTGCACAACGA | 98 |
| PRIMER_2 | chr23:23027620-23028300 | TCATTCCACCAGCAATGTGT | 99 | GGCCACTGCAGAAGAAAGAG | 100 |
| PRIMER_3 | chr23:23048139-23048767 | CTGTTGTCCCAGCCCTGTAT | 101 | AGGTGAGTCCAGGCTAGCAA | 102 |
| DMRT2exon1 | chr23:23055803-23056469 | GAGCCCGAGCGGATAATACT | 103 | ATTAGGACCGCACAGGACAC | 104 |
| DMRT2exon2 | chr23:23056584-23057237 | GCGGCTAGGGTGGTACTTCT | 105 | CTCGTCCTCGTCCTCGTC | 106 |
| DMRT2_GAP | chr23:23057214-23057971 | GAGGACGACGAGGACGAG | 107 | CCACTTTCAAGGCCTCTCTG | 108 |
| DMRT2exon2GAP | chr23:23057214-23057971 | GAGGACGACGAGGACGAG | 109 | CCACTTTCAAGGCCTCTCTG | 110 |
| DMRT2exon3 | chr23:23059113-23059736 | CTGGGGTGACTCTAGCAAGG | 111 | TCACACCAAGGCAAATTTCA | 112 |
| DMRT2exon4.1 | chr23:23061639-23062293 | CCCCCAAAGGGAACTATTTT | 113 | GAACTGAGGTGGTGGCATTT | 114 |
| DMRT2exon4.2 | chr23:23062130-23062788 | TTCAGGGTCTGGGAATATGG | 115 | TCCAACTTGTTTGGCTACGA | 116 |
| DMRT2exon4.3 | chr23:23062686-23063285 | GGCCCCTAAGAAACACAGAG | 117 | CCTGTAGACCCCAGAGACCA | 118 |
| PRIMER_4 | chr23:23067103-23067766 | GGTCCAAATTGTAGGGCTGA | 119 | TTCCCCAGGAGGTTCTCTTT | 120 |
| PRIMER_5 | chr23:23069404-23070095 | CCAGATCAAGGGGAATGCTA | 121 | CAAGGCAGACCAATCCATTT | 122 |
| PRIMER_6 | chr23:23076510-23077194 | CAAAGTAAGCATCCCCAGGA | 123 | GCAGCACCTCTTTCCTCATC | 124 |
| PRIMER_7 | chr23:23080154-23080820 | TGGAAATTTTGGGCTGTTTC | 125 | TTTCTCCAGGGAATTTGTGC | 126 |
| PRIMER_8 | chr23:23085336-23086005 | GCTGCTGGAGACCAGAAAAG | 127 | CGAAGGGCACCTATTCAAAA | 128 |

In Depth Genome Resequencing.

DNA samples from two Icelandic horses, one female mutant DMRT3 homozygote and one male control (homozygous wild-type) were prepared for sequencing. Illumina paired-end libraries were generated from these DNA samples (mean insert sizes of approximately 220 bases). The two libraries were sequenced (2×100 bp) on seven and five lanes, respectively, using an Illumina HiSeq instrument. The reads were mapped to the horse genome (EquCab2 reference assembly) using the software BWA, and PCR-duplicates were removed using the software Picard (http://picard.sourceforge.net). The average read depth obtained for each sample was approximately 30×. SNPs and small insertions/deletions were called from the mapping data after subjecting the alignments to realignment around indels and then variant calling using the Genome Analysis Toolkit (GATK). The variant calls were subjected to recommended VariantFiltrationWalker filters for SNPs listed in the GATK wiki page (http://www.broadinstitute.org/gsa/wiki/index.php/The_Genome_Analysis_Toolkit) and read alignments overlapping SNP and insertion/deletion calls within the 438 kb Gait locus were then manually reviewed to remove obvious artifact calls. Read depths observed in one kilobase windows were used to call candidate duplications in the minimum IBD region, and mapping distances and orientations between paired reads were used to detect structural variations in relation to the reference assembly. The software ANNOVAR was used to annotate SNPs in relation to Ensembl genes.

SNP Analysis Using TaqMan Assays.

TaqMan assays were designed to screen the SNPs at chromosome 23, nucleotide position 22,967,656 (BIEC2_620109; the SNP included in the Illumina SNP panel showing the strongest association to the phenotype) and at nucleotide position 22,999,655 (DMRT3.3; the SNP causing a premature Stop codon in DMRT3 exon 2). Custom TaqMan SNP Genotyping assays (Applied Biosystems, Foster City, Calif.) designed for these two SNPs are summarized in Table 3. Probe and primer designs were obtained from the Applied Biosystems web page (http://www5.appliedbiosystems.com/tools/cadt/) using the custom genotyping assays order option. The ABI PRISM 7900 HT sequence detection system for 384-well format (Applied Biosystems, Foster City, Calif.) was used for the analysis.

TABLE 3

Description of TaqMan assays for SNPs at nucleotide positions 22,967,656 (BIEC2_620109) and 22,999,655 (DMRT3.3) on horse chromosome 23.

| | | SEQ ID NO |
|---|---|---|
| BIEC2_620109 | | |
| Forward Primer Seq. | GCAAAGTGCAGAAATAGTCTTTTGGA | 26 |
| Reverse Primer Seq. | CACTCTTTTGGAATGGTTCACATTAAGG | 27 |
| Reference allele* | C | |
| Reporter Sequence (FAM) | TAGTGCAAACGGTACGTT | 28 |
| Non-reference allele | T | |

TABLE 3-continued

Description of TaqMan assays for SNPs at nucleotide positions 22,967,656 (BIEC2_620109) and 22,999,655 (DMRT3.3) on horse chromosome 23.

| | | SEQ ID NO |
|---|---|---|
| Reporter Sequence (VIC) | AAATAGTGCAAACAGTACGTT | 29 |
| DMRT3.3 | | |
| Forward Primer Seq. | CCTCTCCAGCCGCTCCT | 30 |
| Reverse Primer Seq. | TCAAAGATGTGCCCGTTGGA | 31 |
| Reference allele* | C | |
| Reporter Sequence (VIC) | CTGCCGAAGTTCG | 32 |
| Non-reference allele | A | |
| Reporter Sequence (FAM) | CTCTGCCTAAGTTCG | 33 |

*according to the EquCab2 assembly (available at www.genome.ucsc.edu genome browser)

Genome-Wide Analysis Reveals a Locus on Horse Chromosome 23 Controlling the Pattern of Locomotion.

Statistical analysis of the SNP-chip data for the 70 Icelandic horses with a phenotypic classification as four-gaited or five-gaited was carried using PLINK; 39,695 SNPs passed the quality control. A chi-square test was performed for each marker separately in order to test for a significant difference in genotype frequencies between four-gaited versus five-gaited horses. A genetic model assuming a recessive mode of inheritance was used. Ten thousand permutations were used to correct for multiple testing. The statistical analysis revealed a highly significant association between a SNP (BIEC2_620109, SEQ ID NO: 5) at nucleotide position 22,967,656 base pair on horse chromosome 23 and the gait phenotype (P=0.0002, genome-wide significance; FIG. 1). The two SNPs immediately flanking the highly associated SNP were located at nucleotide positions 22,628,976 (BIEC2-619907, SEQ ID NO: 6) and 23,315,071 (BIEC2-620244, SEQ ID NO: 7) and these showed only weak associations to the phenotype (P=0.01 for the SNP at position 22,628,976 base pair and P=0.32 for the SNP at position 23,315,071 base pair). This result demonstrated that one or more sequence polymorphisms controlling the pattern of locomotion is located in the vicinity of the SNP at position 22,967,656 base pair (the most associated SNP) and within the interval defined by the flanking markers at positions 22,628,976 and 23,315,071 base pairs showing a significantly weaker association to the gait phenotype. This region spans 686 kilo base pairs and five genes are located in the interval ANKRD15, DMRT1, DMRT3, DMRT2 and GTF2A2 (FIG. 2). This locus was named the Gait locus and the results were consistent with a recessive inheritance of the allele associated with the ability to pace, while the wild-type allele (Non-pace) at this locus was dominant.

Resequencing of Selected Regions Refine the Localization of the Gait Locus.

A number of amplicons (Table 2) from the genomic region harbouring the Gait locus as defined by the genome-wide screen (from nucleotide position 22,628,976 to position 23,315,071 on chromosome 23) were resequenced in a small set of four-gaited and five-gaited horses in order to refine the localization of the *Gait locus*. All the sequence polymorphisms detected in this analysis are summarized in Table 4. The results showed that there is a distinct haplotype associated with the recessive gait allele and that the haplotype block showing a complete association to gait in this breed breaks up at nucleotide position 22,877,015 just upstream of the DMRT1 gene. The results refine the localization of the *Gait locus* to the interval from nucleotide position 22,877, 015 base pair to position 23,315,071 base pair; ANKRD15 is located outside the critical interval for Gait.

pace (FIG. 3). Thus, the gait allele is predicted to encode a truncated form of the DMRT3 protein (SEQ ID NO: 4) lacking the last 174 amino acids, reducing the total size of the protein from 474 to 300 amino acids. Full length wild-type horse DMRT3 is shown as SEQ ID NO: 2. An alignment of the part of the DMRT3 protein including the mutated amino acid position 301 (Serine) in horses shows that this protein is highly conserved among vertebrates including fish, bird and mammalian species (FIG. 4).

TaqMan assays were designed for the polymorphisms at nucleotide positions 22,967,656 (the most significantly asso-

TABLE 4

Sequence polymorphisms detected by resequencing amplicons from the genomic region harbouring the Gait locus on horse chromosome 23

| | | Phenotype | | | | | | | | | |
|---|---|---|---|---|---|---|---|---|---|---|---|
| | | Four-gaited | | | | Five-gaited | | | | | |
| SNP | Position | Horse 1 | Horse 2 | Horse 3 | Horse 4 | Horse 5 | Horse 6 | Horse 7 | Horse 8 | Horse 9 | Horse 10 | Horse 11 |
| ANKRD15.1 | 22,793,939 | GG | GC | GC | GG | GG | GG | GG | GG | GG | GG | GG |
| ANKRD15.2 | 22,810,322 | GG | GA | GA | GG | GA | GG | GA | GG | GG | GG | GA |
| ANKRD15.3 | 22,812,345 | GG | GT | GT | GG | GT | GG | GT | GG | GG | GG | GT |
| ANKRD15.4 | 22,812,251 | TT | TT | TT | TT | TC | TT | TC | TT | TT | TT | TC |
| ANKRD15.5 | 22,818,132 | TT | CT | CT | TT | CT | TT | CT | TT | TT | TT | CT |
| ANKRD15.6 | 22,818,158 | GG | GA | GA | GG | GA | GG | GA | GG | GG | GG | GA |
| ANKRD15.7 | 22,821,872 | CC | CA | CA | CC | CA | CC | CA | CC | CC | CC | CA |
| ANKRD15.8 | 22,821,884 | GG | GG | GG | GG | CG | GG | CG | GG | GG | GG | CG |
| SNP.1 | 22,868,190 | nt | nt | CC | CC | nt | nt | nt | nt | CC | CC | CT |
| SNP.2 | 22,868,678 | nt | nt | GA | AA | nt | nt | nt | nt | AA | AA | GA |
| SNP.3 | 22,872,820 | nt | nt | GG | GG | nt | nt | nt | nt | GG | GG | GC |
| SNP.4 | 22,876,848 | nt | nt | CA | AA | nt | nt | nt | nt | AA | AA | AA |
| SNP.5 | 22,877,015 | nt | nt | TT | TT | nt | nt | nt | nt | TT | TT | CT |
| BIEC2_620109 | 22,967,656 | CC | CC | CC | CT | TT | TT | TT | TT | TT | TT | TT |
| DMRT3.1 | 22,986,593 | TT | TT | TT | CT | CC | CC | nt | nt | CC | CC | CC |
| DMRT3.2 | 22,987,143 | CC | CC | CC | CT | TT | TT | nt | nt | TT | TT | TT |
| DMRT3.3 | 22,999,655 | CC | CC | CC | CA | AA | AA | nt | nt | AA | AA | AA |
| DMRT3.4 | 22,999,665 | GC | GG | GG | GC | CC | CC | nt | nt | CC | CC | CC |
| SNP.6 | 23,009,648 | nt | nt | AA | AT | nt | nt | nt | nt | TT | TT | TT | nt = not tested

A Nonsense Mutation Located in Exon 2 of DMRT3 Shows Complete Concordance with the Ability to Pace.

The critical interval for the *Gait locus* comprises the four genes DMRT1, DMRT2, DMRT3 and GTF2A2. The DMRT genes belong to a family of transcription factors that contains the zinc-finger like DNA binding DM domain (Murphy et al. 2007. Vertebrate DM domain proteins bind similar DNA sequences and can heterodimerize on DNA. *BMC Mol. Biol.* 8:58). We sequenced most of the DMRT exons in this region and identified a small number of sequence polymorphisms (Table 4). One of these (DMRT3.3), located in exon 2 of DMRT3 at nucleotide position 22,999,655, caused a nonsense mutation in the allele associated with the ability to ciated SNP in the GWA analysis) and at position 22,999,655 (the mutation in DMRT3 creating a premature Stop codon). These were used to screen all 70 Icelandic horses included in this study. Both SNPs showed complete association between homozygosity for the non-reference allele at both loci and the phenotype (Table 5), the statistical support for an association was overwhelming ($P=6.73 \times 10^{-10}$ for both SNPs, Fisher's Exact Test). The results imply that there is very strong linkage disequilibrium between these two SNPs in the studied population, the two SNPs are located 32 kilo base pairs apart. Nine animals that were classified as four-gaited were homozygous for the haplotype associated with the gait allele (Table 5). These animals were either misclassified by their owners, which is fully possible, or the Gait genotype shows incomplete penetrance due to interaction with environmental factors (for instance training) or other unknown genetic factors.

We tested 2 North-Swedish Trotters and 61 Swedish Standardbred horses (both used for harness racing in Sweden) to investigate if the gait allele is present in other horse breeds. We found that both the 2 North-Swedish Trotters and 59 Standradbred horses were homozygous for the DMRT3 nonsense mutation at nucleotide position 22,999,655 on horse chromosome 23 while the remaining 2 Standardbred horses were heterozygous A/C. The high frequency of this allele in these breeds strongly suggests that the mutation has a favourable effect on the ability to trot at a fast speed. Indeed, the two horses identified as being heterozygous for the gait allele were also considered as being poor trotters. We predict that the gait allele is present at a high frequency in most, if not all, gaited horse breeds as well as horses used for harness racing.

TABLE 5

Highly significant association between SNPs at nucleotide position 22,967,656 (BIEC2-620109) and 22,999,655 (DMRT3.3) on horse chromosome 23 in relation to the phenotypic classification of Icelandic horses as four-gaited or five-gaited. Statistics was calculated using Fisher exact test, with the Gait allele as the recessive allele.

| MARKER | | BIEC2-620109 | DMRT3.3 |
|---|---|---|---|
| Allele 1 ($A_1$) | | C | C |
| Allele 2 ($A_2$) | | T | A |
| Wild-type | $A_1/—$ | 21 | 21 |
| | $A_2/A_2$ | 9 | 9 |
| Five-gaited | $A_1/—$ | 1 | 1 |
| | $A_2/A_2$ | 39 | 39 |
| p | | 6.73E−10 | 6.73E−10 |
| OR | | 83.18 | 83.18 |

OR = odds ratio.
$A_1/— = A_1/A_1$ or $A_1/A_2$

TABLE 6

Genotype distribution for a nonsense mutation (A) in DMRT3 among horse populations.

| Breed | Number | CC | CA | AA |
|---|---|---|---|---|
| Icelandic Horse | 70 | 0.01 | 0.30 | 0.69 |
| Standardbred Trotter | 61 | 0.00 | 0.03 | 0.97 |
| Cold Blooded Trotter | 2 | 0.00 | 0.00 | 1.00 |

TABLE 7

SNP sequences

| SEQ ID NO | sequence | SNP | position |
|---|---|---|---|
| SEQ ID NO: 5 | TTGTTGGGGTCTTATGCAAAGTGCAGAAATAGTCTTTTGGA AAAACGTAC[C/T]GTTTGCACTATTTTCTTATTTCTATTCACC CTTAATGTGAACCATTCCAA | BIEC2_620109 | 22 967 656 |
| SEQ ID NO: 6 | AGAAATGATATATAAAAATTACGAATGCCTCTTAGACAGAAT CCTTATGT[A/G]TGGCACAGAAGTATTTAGTTCGCTTAACAG ATATTGAGTGCTTATATGAG | BIEC2-619907 | 22 628 976 |
| SEQ ID NO: 7 | CTCTTCCTTGCATCCTATCCCCCTAGTGTCGCAAGGGAAGT TGTGAGAGA[C/T]GAGCTTGTAGATCTGCTCTAGAAAATAG GCCTGTTTTCTTAAGAAACCGT | BIEC2-620244 | 23 315 071 |
| SEQ ID NO: 8 | CAGAGTGCCGGTCTGTGGCTGTGGGCGCTGACGAGCACA TGGACAACATT[G/C]TCGTGTACCACAGGGGCTCCAGGTCC TGTAAGGATGCTGCTGTGGGGACA | ANKRD15.1 | 22 793 939 |
| SEQ ID NO: 9 | AGAACTCATTCAAAACCACCAGGCTTACTAGGCTTTTTTAA ATAGACTTG[A/G]CTTTGAACTTCTAAGTGCAGGATCTAAAA CCACTGGCGAAATTTCTGGAA | ANKRD15.2 | 22 810 322 |
| SEQ ID NO: 10 | TTACCTGCATGCCTCTCCCCCTAAACCATTTCTAGCATGTG TGGGCAGAG[T/G]GGGCATCGTGCTGCCCTGCTCACTGGA TCACTCTGGGAACGTTTCCTTCA | ANKRD15.3 | 22 812 345 |
| SEQ ID NO: 11 | AAGGATATGGTGAGTCTGACCTACAGACACTGTCCCCGGT CTGTACAAAG[T/C]GCCCAAGTGGTGACAAAGCATCCCTCG CCTGCCCCCTGAGCTGTTACCTG | ANKRD15.4 | 22 812 251 |
| SEQ ID NO: 12 | AACGCCAAAGCCAGCCAGGTGACTGCGCTTGCTTCCTGGG CTCATGCTCA[C/T]ACTGCTGTGACCCGCACAGGTGCCCAC GCCACACTTCCCACCGCTCGGCA | ANKRD15.5 | 22 818 132 |
| SEQ ID NO: 13 | GCTTGCTTCCTGGGCTCATGCTCACACTGCTGTGACCCGC ACAGGTGCCC[A/G]CGCCACACTTCCCACCGCTCGGCACT CACTCATGGCCCAGCCCCGAGTCC | ANKRD15.6 | 22 818 158 |

TABLE 7-continued

SNP sequences

| SEQ ID NO | sequence | SNP | position |
|---|---|---|---|
| SEQ ID NO: 14 | ACTGAATGTATACATTTTGTGCCTGAACTCACCAGCAAACA GAAGGCAGA[A/C]AACCAAGGGTTGAAGGCTGGAGCTGTC ACAGTAGAAGTTGAGCCAGCAGG | ANKRD15.7 | 22 821 872 |
| SEQ ID NO: 15 | CATTTTGTGCCTGAACTCACCAGCAAACAGAAGGCAGAAA ACCAAGGGTT[G/C]AAGGCTGGAGCTGTCACAGTAGAAGTT GAGCCAGCAGGAATTTGCTGGCC | ANKRD15.8 | 22 821 884 |
| SEQ ID NO: 16 | TCACTCTAATCAAGTTGCTATCACCATTCACACAATTGTCCA GGATAGTA[C/T]TGGGACCCCAGAAAGATCACGCCGCTCCA TTCCCATTTCCCACTTGTTCC | SNP.1 | 22 868 190 |
| SEQ ID NO: 17 | CTGGGCTGAAACAGGTGGTCCTGCTTTCCCCGCCTGCCTG GTCAGGCTGC[G/A]CTCTTCTCCCCTCCCCAGGCTTAAGTC ACTTCATGCAGAACCCTTTATAC | SNP.2 | 22 868 678 |
| SEQ ID NO: 18 | CCAGCATTCTCCGCTTTCAACTTTCTCCCGCTCCTCCAATC CAAACTGGA[G/C]TTAGCATCAGCTACCCACAATGATCAAG CATTTTCTGTGTGGCAGGCCTG | SNP.3 | 22 872 820 |
| SEQ ID NO: 19 | AGGCAAGAAGCGATAGGCAAAAGGCAGCAAGAGCTGGAC CTGCAGATTTG[C/A]AAGTTCTCTGGAGCCAGTAGGTGGAA ACCTCATCAGCAAATGAACGCAGG | SNP.4 | 22 876 848 |
| SEQ ID NO: 20 | CCACACTGAGAGTCTTATTTGCTGATAGAAATGCAGAGACT TCTCTTTTC[T/C]GAGGCTTTCAACCTCGTACTTAATTCTCCT AAGTGAGAAAGAAACCACTC | SNP.5 | 22 877 015 |
| SEQ ID NO: 21 | ACCAGCGGGAGACTGAGGCTGCGAGCGCCGCAAAGACGG GTGCCGCATCT[C/T]TGGCCAGCCCGGAGCGCACGCGGCC GCCGGAGCTGCGGGACCAAGGACCG | DMRT3.1 | 22 986 593 |
| SEQ ID NO: 22 | CCGTCTCAGCCGCCGCCGCCGCAGCGTCCCGCCGCCGAG TTGGCTGCGGC[C/T]GCCGCGCTGCGCTGGGCCACCGAGC CGCAGCCCGGGGCGCTGCAGGCGCA | DMRT3.2 | 22 987 143 |
| SEQ ID NO: 23 | GGAGGTCCTCCTCTCCAGCCGCTCCTCGGCCTCGGCCGC CGACCGAACTT[C/A]GGCAGAGCCCGAGAGCCTCGTGTTG CCCTCCAACGGGCACATCTTTGAAC | DMRT3.3 | 22 999 655 |
| SEQ ID NO: 24 | CTCTCCAGCCGCTCCTCGGCCTCGGCCGCCGACCGAACT TCGGCAGAGCC[C/G]GAGAGCCTCGTGTTGCCCTCCAACG GGCACATCTTTGAACACACCTTGAG | DMRT3.4 | 22 999 665 |
| SEQ ID NO: 25 | GGCCTGGCCCCTAGGGCATTGAAGGGCTGGGGAGAGTCA CATGTACTCCC[A/T]CTGTGGCCTGAAGACCTACCTGGAGG GAAACCAGCTTGCTTAGGGGGCCT | SNP.6 | 23 009 648 |

TABLE 8

Sequence variants on horse chromosome 23 showing strong genetic association with the Gait mutation in horses. The Gait mutation occurs on horse chromosome 23, nucleotide position 22,999.655 bp and is indicated in bold italics below.

| Type | Location/ consequence[1] | Coordinate (EquCab2) | Ref. Allele[2] | Var. allele(s)[3] | Type | Location/ consequence[1] | Coordinate (EquCab2) | Ref. Allele[2] | Var. allele(s)[3] |
|---|---|---|---|---|---|---|---|---|---|
| SNP | intronic | 22919878 | A | G | SNP | intronic | 22926188 | T | C |
| SNP | intronic | 22920361 | C | T | SNP | intronic | 22926872 | A | C |
| SNP | intronic | 22920434 | A | T | SNP | intronic | 22927387 | C | T |
| SNP | intronic | 22920646 | G | A | SNP | intronic | 22927607 | T | C |
| SNP | intronic | 22920717 | C | T | SNP | intronic | 22928220 | C | T |
| SNP | intronic | 22921203 | G | T | SNP | intronic | 22928537 | T | G |
| SNP | intronic | 22922079 | A | G | SNP | intronic | 22928587 | A | G |
| SNP | intronic | 22922780 | C | T | SNP | intronic | 22929137 | G | A |
| SNP | intronic | 22923569 | A | G | SNP | intronic | 22930011 | A | C |
| SNP | intronic | 22924120 | G | A | SNP | intronic | 22932024 | G | A |
| INDEL | intronic | 22924142 | — | A | SNP | intronic | 22932895 | A | G |
| SNP | intronic | 22924299 | T | G | SNP | intronic | 22933218 | A | G[4] |
| SNP | intronic | 22924380 | A | G | SNP | intronic | 22936034 | A | G |
| SNP | intronic | 22924407 | C | T | SNP | intronic | 22940759 | T | G |
| SNP | intronic | 22926098 | C | T | SNP | intronic | 22942423 | T | A |

TABLE 8-continued

Sequence variants on horse chromosome 23 showing strong genetic association with the Gait mutation in horses. The Gait mutation occurs on horse chromosome 23, nucleotide position 22,999.655 bp and is indicated in bold italics below.

| Type | Location/ consequence[1] | Coordinate (EquCab2) | Ref. Allele[2] | Var. allele(s)[3] |
|---|---|---|---|---|
| SNP | intronic | 22945643 | G | C |
| SNP | intronic | 22946599 | A | T |
| SNP | intronic | 22948774 | C | T |
| SNP | intronic | 22949055 | A | G |
| SNP | intronic | 22949108 | A | G |
| SNP | intronic | 22949240 | T | C |
| SNP | intronic | 22949710 | A | G |
| SNP | intronic | 22956846 | G | T |
| SNP | intronic | 22960132 | A | C |
| SNP | intronic | 22960528 | T | C |
| SNP | intronic | 22960710 | C | T |
| SNP | intronic | 22964042 | C | T |
| INDEL | intronic | 22965059 | — | GA |
| SNP | intronic | 22967119 | C | T |
| SNP | intronic | 22967656 | C | T |
| SNP | intronic | 22967915 | G | C |
| SNP | intronic | 22968898 | G | A |
| SNP | intronic | 22973984 | C | T |
| SNP | intronic | 22974589 | T | C |
| SNP | intergenic | 22979124 | T | C |
| SNP | intergenic | 22980014 | C | T |
| SNP | intergenic | 22982879 | T | C |
| INDELs | intergenic | 22984588 | A | — |
| INDEL | intergenic | 22985746 | G | — |
| SNP | intronic | 22988210 | C | A |
| SNP | intronic | 22988991 | T | G |
| SNP | intronic | 22993092 | C | A |
| SNP | intronic | 22994591 | C | A |
| SNP | intronic | 22999058 | G | A |
| *SNP* | *stopgain SNP* | *22999655* | *C* | *A* |
| SNP | intergenic | 23002606 | A | G |
| INDEL | intergenic | 23003956 | — | TG |
| SNP | intergenic | 23008772 | G | A |
| SNP | intergenic | 23008789 | G | A |
| SNP | intergenic | 23009648 | A | T |
| SNP | intergenic | 23010164 | G | A |
| SNP | intergenic | 23011289 | G | C |

[1]Location: Indicates where the SNP is located in relation to Ensembl genes. In cases of coding sequence overlap, the predicted consequence to the protein is indicated. The gene intersection was performed using the software ANNOVAR.
[2]Ref. allele. This is the reference allele in the horse genome assembly (EquCab2).
[3]Var. allele: This is the variant allele at polymorphic position showing very strong association with the Gait mutation. For insertion polymorphisms in relation to the reference assembly (EquCab2), the reference allele is denoted "—" and for deletions in relation to the reference the variant allele is denoted "—". The sequenced mutant horse was homozygous for the variant allele at all sites except one (see Footnote 4) listed in this table unless otherwise stated in the Var. allele column.
[4]This SNP was identified as heterozygous (AG) in the mutant horse and homozygous for the reference allele in the control horse. The G-allele at this SNP has likely occurred subsequent to the DMRT3 nonsense mutation.

Electrophoretic Mobility Shift Assays (EMSA).

The oligonucleotide 5'-ggatccTCGAGAACAATGTAACAATTTCGCCC-3'(SEQ ID NO: 34) and its complementary sequence were annealed in 10 mM Tris pH 7.5, 1 mM EDTA, 50 mM KCl by firstly heating to 95° C. for 2 min and thereafter cooled to 25° C. (2 min/degree). The duplex was labelled with Klenow DNA polymerase and [α-32P]-dCTP and purified using a Bio-Rad Micro Bio-Spin 30 column. DMRT3 wild type and mutant protein were produced by in vitro-translation using a TNT Quick Coupled Transcription/Translation System (Promega). EMSA was performed as described by Culbertson & Leeds, 2003 (*Looking at mRNA decay pathways through the window of molecular evolution. Curr. Opin. Genet.* Dev. 13, 207-214) with the following modifications. No plasmid DNA was added and 1.0 µl in vitro-translated protein and 150× cold competitor were used. The reaction mixture was incubated on ice for 20 min before adding the radioactive oligo and thereafter incubated at room temperature for 30 min. Gels were run at 150 V in room temperature. Both full-length wild-type and mutant DMRT3 protein were found to bind a previously defined DMRT-binding motif (FIG. 6). Thus, the DMRT3 mutation does not lead to an altered expression pattern and the mutant protein appears to maintain its cellular localization and DNA binding profile. It may therefore be a dominant negative form with normal DNA-binding but defective interaction with other proteins. This would be consistent with the clear phenotypic effects observed in heterozygotes. However, the mutation is not fully dominant as CA heterozygotes and AA homozygotes show distinct phenotypic differences.

CONCLUSIONS

We have presented abundant evidence that the DMRT3_Ser301STOP mutation has a major effect on gaits in horses. Our interpretation of the phenotypic consequences of this mutation is that homozygosity for the mutation is required but not sufficient for pacing, as many Standardbred Trotters and some Icelandic horses that are homozygous mutant do not pace. On the other hand heterozygosity or homozygosity for the mutation are permissive to enable a variety of four-beat ambling gaits to be performed, with genetic modifiers that may be unique to each gaited breed. The mutation promotes ambling gaits and pace and it inhibits the transition from trot or pace to gallop, which explains its high frequency in pacers and trotters used for harness racing. It is an open question if the mutation alters the fate of DMRT3-neurons or changes their transcriptional regulation, but it is clear that these neurons must have a key role for the control centre in the spinal cord coordinating limb movements.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of breeding horses, the method comprising the steps of:
   extracting DNA from each sample obtained from a plurality of horses;
   determining in each extracted DNA sample the presence or absence of a nonsense mutation in exon 2 of the equine DMRT3 gene at nucleotide position 22,999,655 on horse chromosome 23, said nucleotide position corresponding to nucleotide position 939 in SEQ ID NO:3, and position 51 in SEQ ID NO:23, wherein the nucleotide position on horse chromosome 23 refers to the horse reference sequence according to the September 2007 *Equus caballus* draft assembly EquCab2;
   selecting a first breeding horse from the plurality of horses comprising one or two A alleles at the nonsense mutation;
   selecting a second breeding horse from the plurality of horses comprising one or two A alleles at the nonsense mutation; and
   breeding the first breeding horse with the second breeding horse.

2. The method according to claim 1, wherein the first and second breeding horses both are homozygous for the nonsense mutation.

3. The method according to claim 1, wherein said nucleotide primer specifically binds to the DNA sequence between nucleotide positions 22,919,878 and 23,011,289 base pairs on the horse chromosome 23.

4. The method according to claim 1, wherein said nucleotide primer specifically binds to the sequences SEQ ID NO:1, 3 and 5-25.

5. The method according to claim 1, wherein said nucleotide primer is selected from SEQ NO:26, SEQ ID NO:27, SEQ ID NO:30, and SEQ ID NO:31.

6. The method according to claim 1, wherein said nucleotide primer specifically binds to the DMRT3 gene.

7. The method according to claim 1, wherein said determining is performed by polymerase chain reaction (PCR), allele specific hybridization, a 3'exonuclease assay, a Taqman assay, fluorescent dye and quenching agent-based PCR assay, allele-specific restriction enzymes (RFLP-based techniques), direct sequencing, the oligonucleotide ligation assay (OLA), pyrosequencing, the invader assay, minisequencing, DHPLC-based techniques, single strand conformational polymorphism (SSCP), allele-specific PCR, denaturating gradient gel electrophoresis (DGGE), temperature gradient gel electrophoresis (TGGE), chemical mismatch cleavage (CMG), heteroduplex analysis based system, techniques based on mass spectroscopy, invasive cleavage assay, polymorphism ratio sequencing (PRS), microarrays, a rolling circle extension assay, HPLC-based techniques, extension based assays, ARMS (Amplification Refractory Mutation System), ALEX (Amplification Refractory Mutation Linear Extension), SBCE (Single base chain extension), molecular beacon assays, invader assays, ligase chain reaction assays, 5'-nuclease assay-based techniques, hybridization capillary array electrophoresis (UAE), solid phase hybridization assays, dot blots, reverse dot blots, and chips.

8. The method according to claim 1, wherein the determining comprises contacting a nucleotide primer that specifically binds to the extracted DNA sequence between nucleotide positions 22,628,976 and 23,315,071 base pairs on horse chromosome 23, or to the complementary strand thereof, with said extracted DNA under hybridizing conditions.

\* \* \* \* \*